United States Patent [19]
Yoon et al.

[11] Patent Number: 6,146,401
[45] Date of Patent: *Nov. 14, 2000

[54] EXPANDABLE MULTIFUNCTIONAL INSTRUMENTS FOR CREATING SPACES AT OBSTRUCTED SITES ENDOSCOPICALLY

[76] Inventors: InBae Yoon; Suzanne J. Yoon; Samuel C. Yoon, all of 2101 Highland Ridge Dr., Phoenix, Md. 21131

[*] Notice: This patent issued on a continued prosecution application filed under 37 CFR 1.53(d), and is subject to the twenty year patent term provisions of 35 U.S.C. 154(a)(2).

[21] Appl. No.: 09/124,046

[22] Filed: Jul. 29, 1998

Related U.S. Application Data

[60] Continuation of application No. 08/572,215, Dec. 13, 1995, Pat. No. 5,865,802, which is a division of application No. 08/369,545, Jan. 6, 1995, which is a continuation-in-part of application No. 07/596,937, Oct. 15, 1990, abandoned, which is a continuation-in-part of application No. 07/222,776, Jul. 22, 1988, abandoned, and a continuation-in-part of application No. 08/249,116, May 25, 1994, Pat. No. 5,514,091.

[51] Int. Cl.[7] .................................................. A61M 29/00
[52] U.S. Cl. ........................ 606/192; 604/264; 604/912; 604/164.01; 604/164.09; 604/916; 606/198
[58] Field of Search ...................................... 600/184, 201, 600/206–209; 606/192, 198; 604/104, 264, 912, 913, 107, 96, 106, 101, 165, 164, 164.01, 101.02, 101.04, 164.03, 164.04, 164.09, 164.1, 164.11, 916, 96.01, 165.01

[56] References Cited

U.S. PATENT DOCUMENTS

| | | |
|---|---|---|
| 716,040 | 12/1902 | Holt . |
| 1,909,967 | 5/1933 | Jones . |
| 3,039,468 | 6/1962 | Price . |
| 3,253,594 | 5/1966 | Matthews et al. . |
| 3,495,586 | 2/1970 | Regenbogen . |
| 3,512,528 | 5/1970 | Whitehead et al. . |
| 3,557,794 | 1/1971 | VanPatten . |

(List continued on next page.)

FOREIGN PATENT DOCUMENTS

| | | |
|---|---|---|
| 0432363 | 2/1991 | European Pat. Off. . |
| 3519626 | 12/1986 | Germany . |

OTHER PUBLICATIONS

"Soft–Wans", Atrraumatic Tissue Manitpulation Balloon, Cabot Medical, 2021 Cabot Boulevard West, Langhorne, PA 19047 USA.

"Expose Retractor, Inflatable Retractor," Advanced Surgical, Inc. 305 Sollege Road East, Princeton, New Jersey 08540, Patent No. 5,308,327.

"Expose Retractor, Reusable Retractor," Advanced Surgical, Inc. 305 Sollege Road East, Princeton, New Jersey 08540, Patent Pending PM70046.

"A Conservative Approach to Laparascopic Hernia Repair", Origin Medsystems, Inc., 135 Constitution Drive, Menlo Park, CA 94025 USA.

"Delivering the Future First in Bladder Neck Suspension Surgery", Origin Medsystems, Inc, 135 Constitution Drive, Menlo Park, CA 94025 USA.

"New Directions in Laparascopy", Origin Medsystems, Inc, 135 Constitution Drive, Menlo Park, CA 94025 USA.

*Primary Examiner*—Corrine McDermott
*Assistant Examiner*—Cris L. Rodriguez
*Attorney, Agent, or Firm*—Blank, Rome, Comisky & McCauley LLP

[57] ABSTRACT

An expandable multifunctional instrument for creating a space at an obstructed site in anatomical tissue in the body including an elongate member having a distal end for being positioned at the obstructed site, a proximal end for being disposed externally of the body and an expandable member at the distal end of the elongate member. The expandable member includes a balloon movable fluidically from a non-expanded position to an expanded position at the obstructed site. The balloon assumes a preformed, predetermined configuration in the expanded position at the obstructed site to separate the anatomical tissue to create a space at the obstructed site.

4 Claims, 13 Drawing Sheets

U.S. PATENT DOCUMENTS

| | | | |
|---|---|---|---|
| 3,598,119 | 8/1971 | White . | |
| 3,833,003 | 9/1974 | Taricco . | |
| 3,882,852 | 5/1975 | Sinnreich . | |
| 3,890,970 | 6/1975 | Gullen . | |
| 3,952,742 | 4/1976 | Taylor | 128/172.1 |
| 4,019,499 | 4/1977 | Fitzgerald . | |
| 4,043,338 | 8/1977 | Homm et al. . | |
| 4,077,412 | 3/1978 | Moossun . | |
| 4,089,337 | 5/1978 | Kronner . | |
| 4,219,026 | 8/1980 | Layton . | |
| 4,230,123 | 10/1980 | Hawkins, Jr. | 128/658 |
| 4,291,687 | 9/1981 | Sinnreich . | |
| 4,312,353 | 1/1982 | Shahbabian . | |
| 4,372,295 | 2/1983 | Heckele . | |
| 4,430,076 | 2/1984 | Harris . | |
| 4,535,773 | 8/1985 | Yoon . | |
| 4,568,326 | 2/1986 | Rangaswamy . | |
| 4,575,371 | 3/1986 | Nordqvist et al. . | |
| 4,607,619 | 8/1986 | Seike et al. . | |
| 4,608,965 | 9/1986 | Anspach, Jr. et al. . | |
| 4,748,982 | 6/1988 | Horzewski et al. . | |
| 4,775,362 | 10/1988 | Kronner . | |
| 4,885,003 | 12/1989 | Hillstead . | |
| 4,909,787 | 3/1990 | Taguschi et al. . | |
| 4,966,583 | 10/1990 | Debbas . | |
| 4,998,527 | 3/1991 | Meyer . | |
| 5,002,557 | 3/1991 | Hasson . | |
| 5,002,558 | 3/1991 | Klein et al. . | |
| 5,007,898 | 4/1991 | Rosenbluth et al. . | |
| 5,041,093 | 8/1991 | Chu . | |
| 5,074,871 | 12/1991 | Groshong . | |
| 5,103,804 | 4/1992 | Abele et al. . | |
| 5,113,846 | 5/1992 | Hiltebrandt et al. . | |
| 5,163,949 | 11/1992 | Bonutti | 606/192 |
| 5,176,128 | 1/1993 | Andrese . | |
| 5,178,133 | 1/1993 | Pena . | |
| 5,183,464 | 2/1993 | Dubrul et al. . | |
| 5,188,630 | 2/1993 | Christoudias . | |
| 5,195,507 | 3/1993 | Bilweis . | |
| 5,197,948 | 3/1993 | Ghodsian . | |
| 5,246,421 | 9/1993 | Saab . | |
| 5,250,025 | 10/1993 | Sosnowski et al. | 604/51 |
| 5,256,139 | 10/1993 | Ghodsian . | |
| 5,269,753 | 12/1993 | Wilk | 604/49 |
| 5,273,026 | 12/1993 | Wilk . | |
| 5,275,610 | 1/1994 | Eberbach . | |
| 5,295,952 | 3/1994 | Pietrafitta . | |
| 5,301,682 | 4/1994 | Debbas . | |
| 5,308,327 | 5/1994 | Heaven et al. . | |
| 5,318,586 | 6/1994 | Ereren . | |
| 5,320,604 | 6/1994 | Walker et al. . | |
| 5,320,605 | 6/1994 | Sahota . | |
| 5,331,947 | 7/1994 | Shturman . | |
| 5,342,306 | 8/1994 | Don Michael | 604/101 |
| 5,345,927 | 9/1994 | Bonutti . | |
| 5,354,270 | 10/1994 | Wilk et al. . | |
| 5,359,995 | 11/1994 | Sewell, Jr. | 128/20 |
| 5,364,356 | 11/1994 | Hofling . | |
| 5,400,770 | 3/1995 | Nakao et al. . | |
| 5,405,360 | 4/1995 | Tovey . | |
| 5,425,357 | 6/1995 | Moll et al. | 128/20 |
| 5,459,175 | 10/1995 | Miller . | |
| 5,514,091 | 5/1996 | Yoon | 604/101 |
| 5,588,951 | 12/1996 | Zhu et al. | 600/207 |
| 5,591,190 | 1/1997 | Yoon . | |
| 5,632,761 | 5/1997 | Smith et al. . | |
| 5,635,223 | 6/1997 | Klieman . | |
| 5,843,017 | 12/1998 | Yoon | 604/22 |

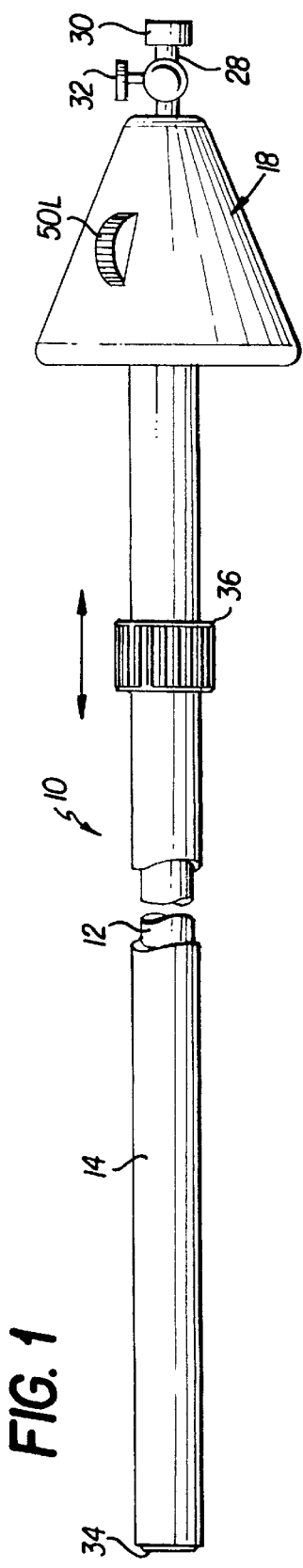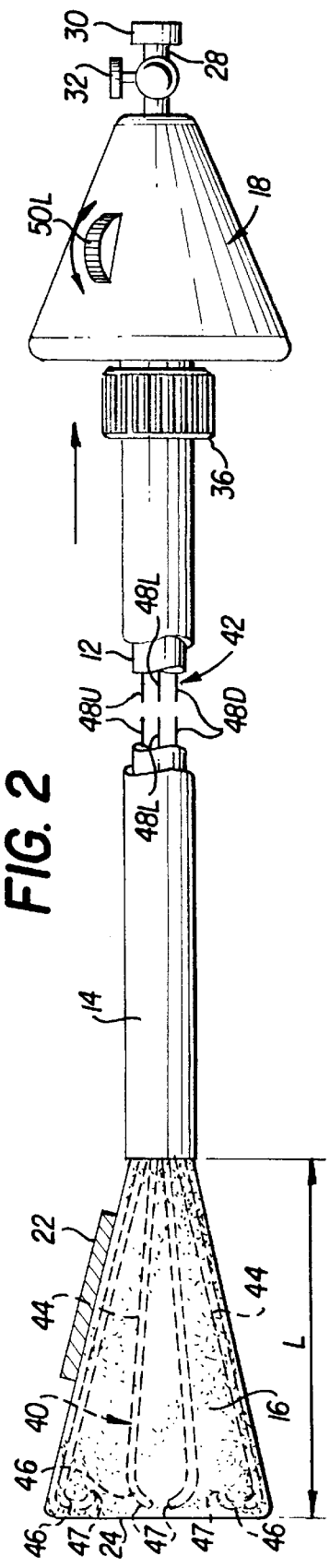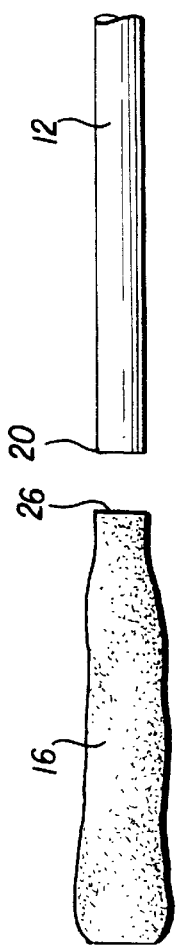

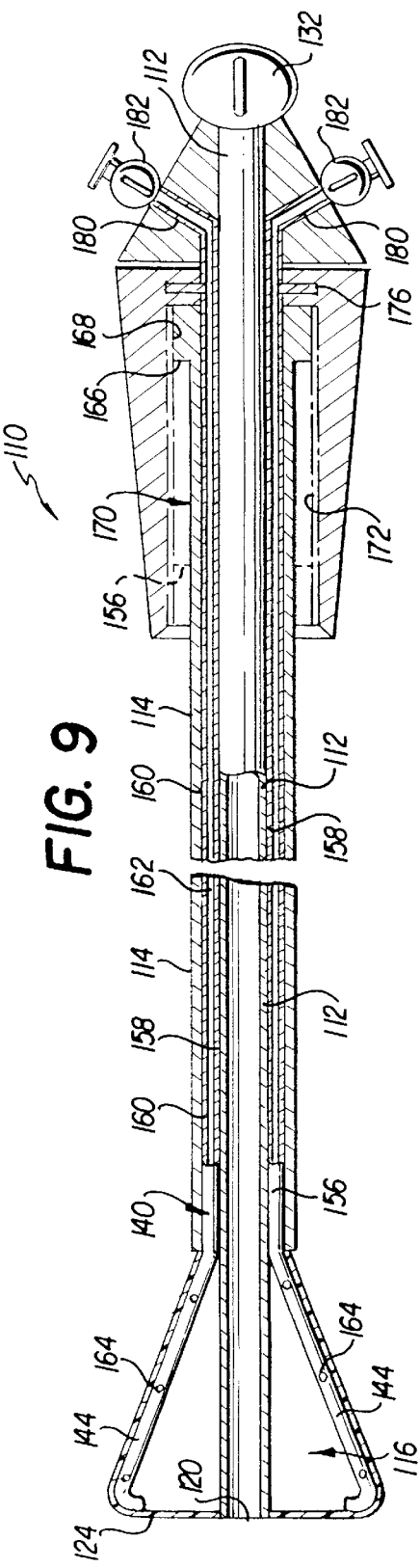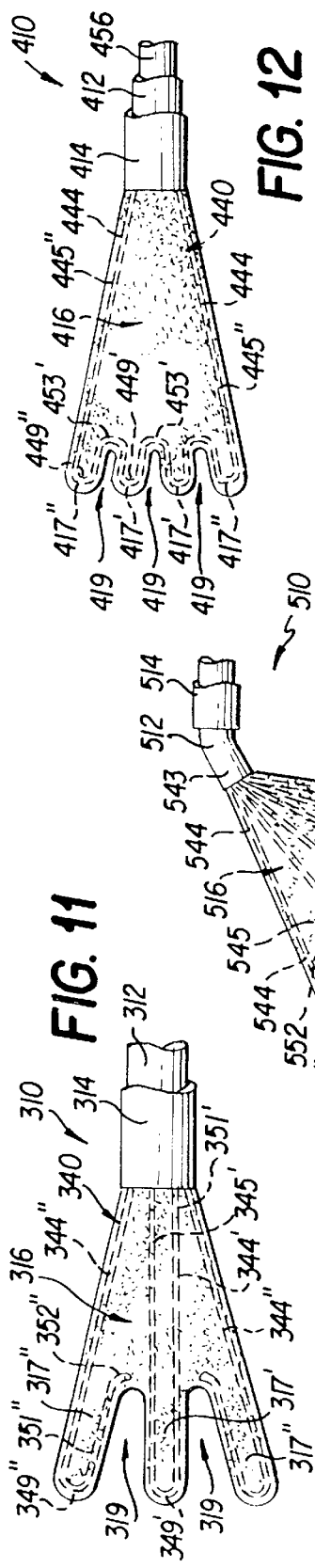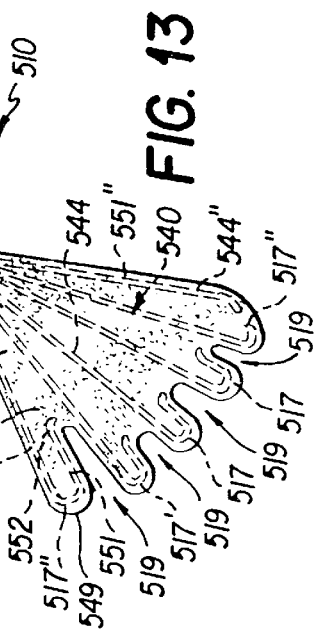

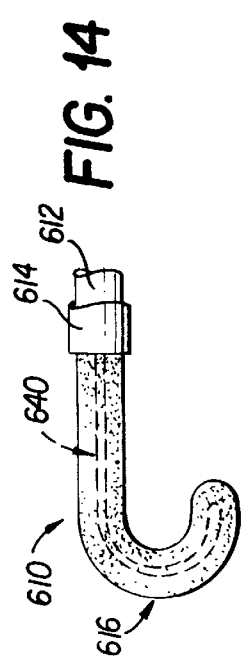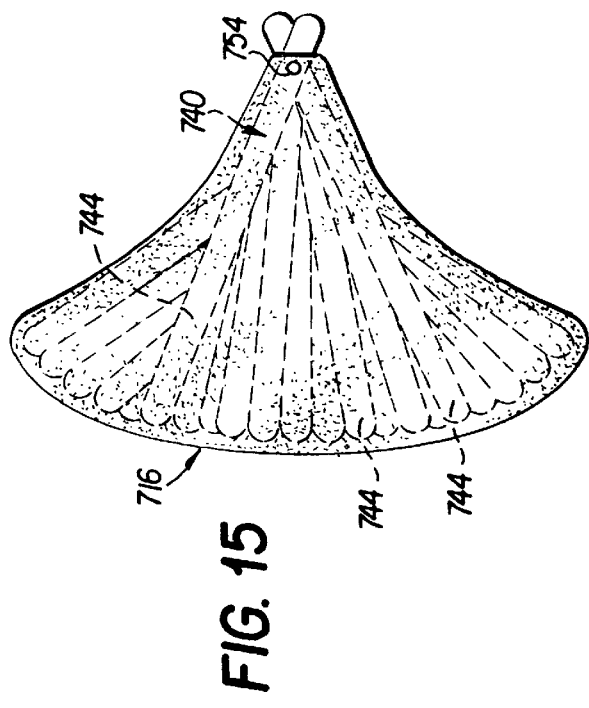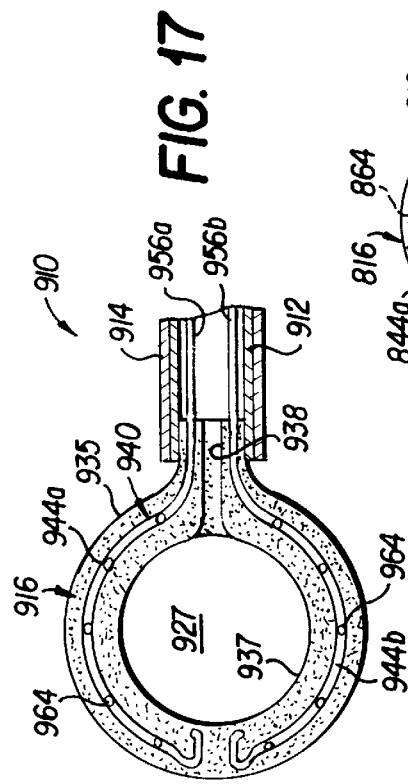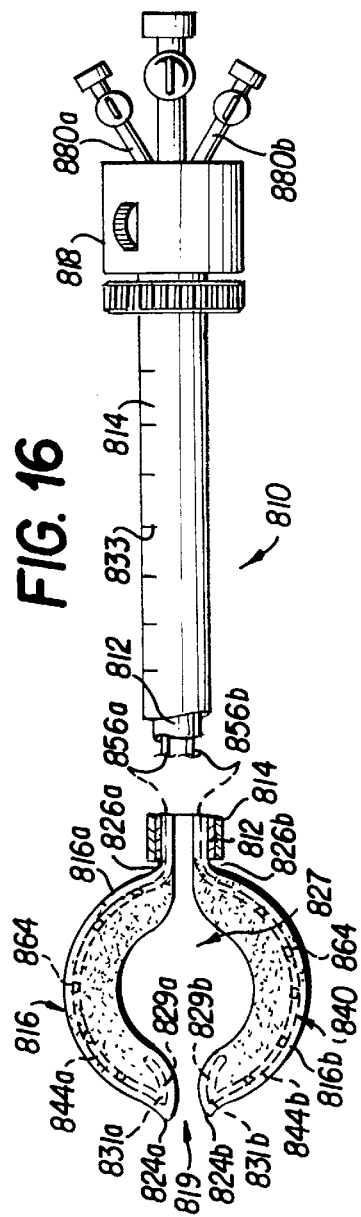

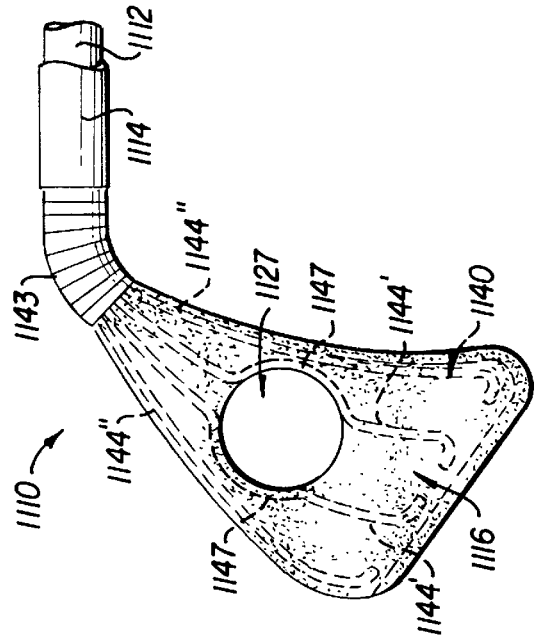
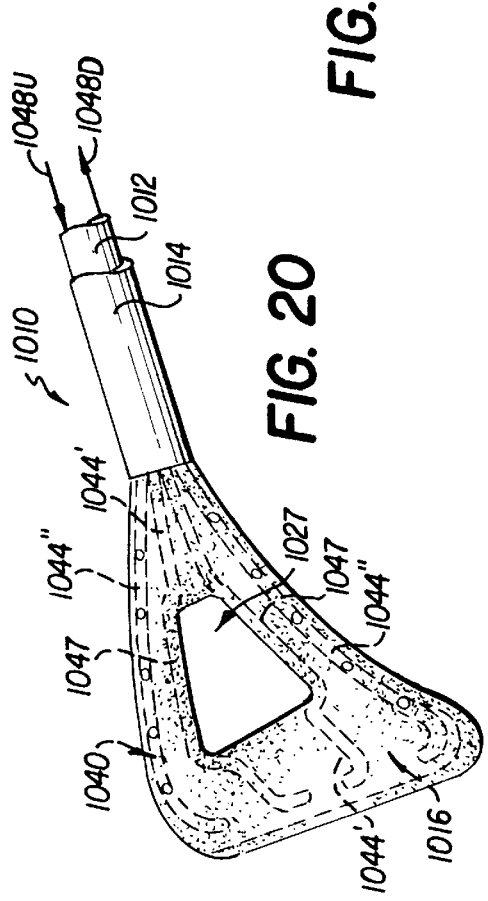
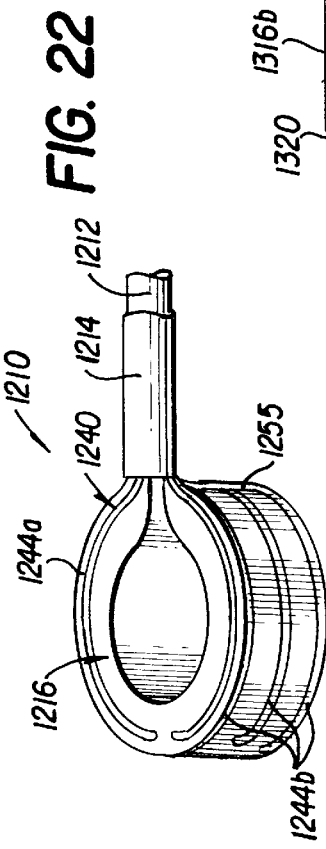
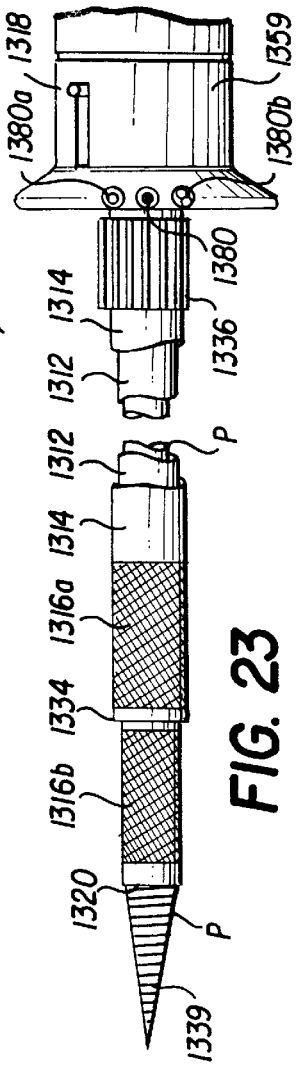

EXPANDABLE MULTIFUNCTIONAL INSTRUMENTS FOR CREATING SPACES AT OBSTRUCTED SITES ENDOSCOPICALLY

CROSS-REFERENCE TO RELATED PATENT APPLICATIONS

This application is a continuation of prior application Ser. No. 08/572,215 filed Dec. 13, 1995, now U.S. Pat. No. 5,865,802 which is a divisional of prior application Ser. No. 08/369,545 filed Jan. 6, 1995, which is a continuation-in-part of Ser. No. 07/596,937 filed on Oct. 15, 1990, now abandoned, which is a continuation-in-part of Ser. No. 07/222,776 filed on Jul. 22, 1988, now abandoned, and is also a continuation-in-part of Ser. No. 08/249,116 filed on May 25, 1994, now U.S. Pat. No. 5,514,091, the disclosures of the aforesaid patent applications being incorporated herein by reference.

BACKGROUND OF THE INVENTION

1. Field of the Invention

The present invention pertains to minimally invasive surgical procedures and, more particularly, to methods and instruments for creating operating spaces to facilitate the performance of minimally invasive surgical procedures.

2. Discussion of the Prior Art

Endoscopic or minimally invasive surgical procedures have become well accepted due to the reduced trauma and recovery time for the patient as well as the associated decrease in hospitalization time and cost. It is desirable to expand the types of procedures that can be performed using minimally invasive techniques; however, for such procedures to be universally accepted, the procedures must be capable of being performed in, at most, the same time required for the same procedure performed by open surgery and must be capable of being performed by surgeons of varying degrees of skill.

There are many areas of surgery to which it would be desirable to extend minimally invasive techniques, and one such area is the treatment of tissue disposed at portions of the anatomy other than in cavities providing sufficient space to perform procedures such as, for example, the abdomen and thorax. The terms "tissue" and "organ structure" are used herein synonymously and include portions or the entireties of all anatomical parts. Examples of such areas of treatment include, for example, preperitoneal hernia repair, bladder neck suspension, excision or biopsy of masses or tumors within anatomical parts such as the breast or the brain, and the like. When procedures are performed in cavities such as the abdomen, conventional retractors or other tissue manipulators can normally be used for exposure of tissue to be treated; however, where the tissue to be treated is located in obstructed anatomical sites such as in very small cavities, in potential cavities such as between layers of anatomical walls, in non-layered tissue or in a single layer of tissue, visualization of the operative site is obstructed as well as is space for maneuvering instruments making minimally invasive surgery extremely difficult to perform in an acceptable manner. As used herein, the term "obstructed site" refers to anatomical spaces or cavities of such a small size that procedures cannot be visualized and/or performed as well as anatomical locations where no space or cavity exists. In the latter case, the obstructed site includes "potential spaces or cavities", such as between layers of anatomical wall that can be separated or spaced such as the peritoneum, fascia and muscles of the abdominal wall and the epidural spaces between the dura matter and the brain and spinal cord, between tissue structure that is normally closed or collapsed as well as locations within homogenous tissue that is not separable on a layer-by-layer or constituent basis such as the breast, the brain and the lung.

SUMMARY OF THE INVENTION

Accordingly, it is a primary object of the present invention to facilitate minimally invasive procedures performed at obstructed anatomical sites by creating operating spaces adjacent tissue to be treated.

Another object of the present invention is to create an operating space adjacent tissue to be treated allowing procedures to be carried out by single puncture techniques as well as multiple puncture techniques.

A further object of the present invention is to encircle tissue to be treated with an expandable member to create an operating space adjacent the tissue to be treated.

An additional object of the present invention is to utilize a plurality of spaced, expandable members to create an operating space for treatment of tissue at an obstructed anatomical site.

The present invention has an additional object in that operating spaces are created at obstructed anatomical sites by expandable members remaining in place during minimally invasive procedures such that insufflation of the space can be accomplished but is not required.

In accordance with the present invention, operating spaces are created at obstructed anatomical sites with the use of expandable members formed by fluid expansible or distensible membranes or balloons, mechanically expandable devices, such as articulated arms or spines returned to a preformed shape upon release of constraints thereon, and/or absorbent materials expandable upon absorption of fluids. Preferably, the outer surfaces of the expandable members are covered with an absorbent material to permit removal of body fluids, such as blood, from the operative site to enhance visualization. Additionally, as disclosed in the prior applications, aspiration of fluids from the absorbent material can be accomplished while the expandable members remain in place. By arranging plural expandable members in spaced relation, the space between the expandable members can define the operating space, and the distance between the expandable members can be adjustable by the use of collars, or by mounting the expandable members on telescoping or sliding tubes, both disclosed in the prior applications. By shaping the expandable members to form an opening or channel therein, the tissue to be treated can be exposed by positioning the expandable members such that the tissue is located in the opening.

The expandable members are constructed in accordance with the tissue in which an operating space is to be created including the angular orientation of the expandable member relative to the longitudinal axis of the instrument and the expansion means. Where preformed spines are used, the expandable members are preferably flat when introduced such that the spines maintain a predetermined shape during positioning of the expandable members and the expandable members are thereafter inflated. The use of a toroid or doughnut shape is particularly advantageous as are multiple finger shapes with openings defined between the fingers.

Other objects and advantages of the present invention will become apparent from the following description of the preferred embodiments taken in conjunction with the accompanying drawings a wherein like parts in each of the several figures are identified by the same reference characters.

BRIEF DESCRIPTION OF THE DRAWINGS

FIG. 1 is a broken side view of an expandable multifunctional instrument according to the present invention.

FIG. 2 is a broken side view, partly in section, of the expandable multifunctional instrument of FIG. 1 with the outer member in a retracted position and the expandable member in an expanded position.

FIG. 3 is an exploded side view of the inner member and the expandable member for the expandable multifunctional instrument of FIG. 1.

FIG. 9 is a broken side view, partly in section, of a modification of an expandable multifunctional instrument according to the present invention.

FIG. 11 is a broken side view of a distal portion of a further modification of an expandable multifunctional instrument according to the present invention having an expandable member defining a three finger shape.

FIG. 12 is a broken side view of a distal portion of an additional modification of an expandable multifunctional instrument according to the present invention having an expandable member defining a four finger shape.

FIG. 13 is a broken side view of a distal portion of another modification of an expandable multifunctional instrument according to the present invention having an expandable member defining a five finger shape.

FIG. 14 is a broken side view of a distal portion of yet another modification of an expandable multifunctional instrument according to the present invention having an expandable member defining a curved J-shape.

FIG. 15 is a broken side view of a modification of an expandable member according to the present invention having a fan-like spine.

FIG. 16 is a broken side view, partly in section, of a further modification of an expandable multifunctional instrument according to the present invention having an expandable member defining a C-shape.

FIG. 17 is a broken side view, partly in section, of a distal portion of an additional modification of an expandable multifunctional instrument according to the present invention having an expandable member defining a toroid shape.

FIG. 20 is a broken perspective view of a distal portion of another modification of an expandable multifunctional instrument according to the present invention.

FIG. 21 is a broken perspective view of a distal portion of a further modification of an expandable multifunctional instrument according to the present invention.

FIG. 22 is a broken perspective view of a distal portion of yet another modification of an expandable multifunctional instrument according to the present invention.

FIG. 23 is a broken side view of a further modification of an expandable multifunctional instrument according to the present invention.

DESCRIPTION OF THE PREFERRED EMBODIMENTS

Figure 4:
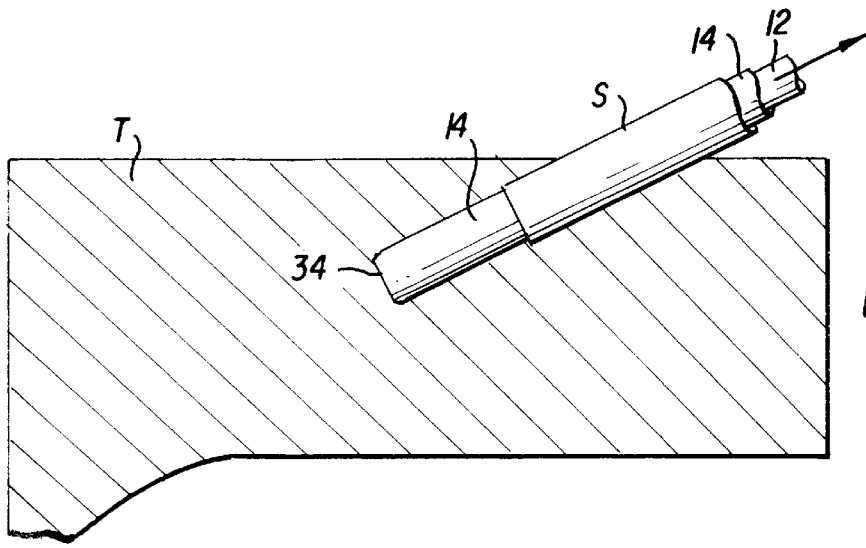
FIG. 4 is a broken perspective view of the expandable multifunctional instrument of FIG. 1 introduced at an obstructed site in anatomical tissue.

An expandable multifunctional instrument 10 according to the present invention, as illustrated in FIGS. 1 and 2, includes an elongate inner tubular member 12, an elongate outer tubular member 14 concentrically disposed around inner tubular member 12, an expandable member 16 and a hub 18 mounting a proximal end of inner member 12. Inner member 12 can be made of any suitable rigid, semi-rigid, flexible or bendable medical grade material, such as metal or plastic, and can have any desirable cross-sectional configuration including cylindrical or tubular configurations in accordance with procedural use. Inner member 12 can be straight, can have a predetermined, curve, bend or angle or can be selectively bent, angled or curved during use as explained further below. Inner member 12 includes a distal end 20, a proximal end mounted to hub 18 and a lumen or internal passage extending longitudinally between the distal and proximal inner member ends.

Expandable member 16 for instrument 10, as shown in FIG. 3, is carried at the distal end 20 of inner member 12 and is formed of one or more layers of material configured to define a body, envelope or bag having a closed distal end 24 and an open proximal end 26 secured to inner member distal end 20 with the inner member lumen in communication with the interior of the expandable member. The expandable member proximal end 26 can be secured to the inner member 12 in many various ways including adhesively or with the use of mechanical seals. The proximal end 26 of expandable member 16 is formed as a tubular neck configured to fit closely over the distal end 20 of inner member 12 for securement thereto along a peripheral or circumferential seal to form a sealed or fluid-tight envelope. Expandable member 16 is movable from a non-expanded or collapsed position, shown in FIG. 3, allowing the expandable member 16 to be received in outer member 14, to an expanded position, shown in FIG. 2, forming an enlargement or protrusion at a distal end of instrument 10. The expandable member 16 can be made of an expandable, distensible, collapsible, flexible, resilient, stretchable or elastic material, such as medical grade silicone or latex rubber or sponge, or of a non-elastic, non-stretchable material, such as plastic. Preferably, the expandable member 16 is made of a tearing or breakage-resistant material and is transparent to permit visualization through the material of the expandable member. The expandable member 16 can have any desirable cross-sectional configuration including various predetermined or preformed shapes. Expandable member 16 for instrument 10 is in the nature of a continuously expandable or inflatable balloon or membrane made of stretchable, elastic material having a predetermined or preformed triangular configuration in side view in the expanded position. The expandable member 16 can have various configurations in end view as disclosed in prior application Ser. No. 08/249,116. A layer, membrane or body 22 can be carried by the expandable member 16 such as along all or part of the external surface thereof as shown in FIG. 2 or within the expandable member as described in prior application Ser. No. 08/249,116. The layer or membrane can be permanently or removably or separably attached to or carried by the expandable member; and, where removable or separable, the membrane can be applied by the instrument to tissue structure or detached from the instrument to be left in the body. The layer 22 can be formed of absorbent material as disclosed in the prior application. The membrane 22 can be formed of or contain an anti-coagulating or anti-adhesion agent or a coagulating agent, it being noted that membranes containing coagulating agents normally dissolve in use whereas membranes containing anti-coagulating agents normally do not dissolve in use but can be absorbed by the body. An example of a membrane containing anti-coagulating or anti-adhesion agents is Interceed marketed by Johnson & Johnson Medical Inc. of Arlington, Tex. Examples of membranes containing coagulating agents include Surgicel and Instat marketed by Johnson & Johnson Medical Inc. of Arlington, Tex. and Avitene marketed by Med Chem Products, Inc. of Woburn, Mass. The membrane can carry medicaments such as antibiotics and chemotherapeutic agents as well as any other agents for application to tissue.

Hub 18 can be made of any desirable material, such as plastic, and can have any desirable configuration including a truncated triangular or conical configuration to facilitate grasping by a surgeon. If desired, the configuration of hub 18 can be selected to correspond to a predetermined configuration of expandable member 16 in the expanded position. A longitudinal passage extends through hub 18 for receiving the proximal end of inner member 12, and the inner member 12 can be permanently or removably secured to hub 18 in many various ways such as adhesively or with the use of threaded connections. An inlet tube or conduit 28 extends into or communicates with the longitudinal passage of hub 18 from externally thereof to communicate with the lumen of inner member 12 providing a working or operating channel through the instrument. Inlet tube 28 terminates proximally at a connector 30 for being coupled with a source or supply of fluid. A valve 32, such as a stop cock, communicates with tube 28 for controlling the flow of fluid to and from expandable member 16. Valve 32 can be designed in many various ways to permit instruments to be introduced through the working channel to close off or seal the working channel when no instrument passes therethrough.

Outer member 14 can be made of any desirable medical grade materials, including metal or plastic, with sufficient rigidity to maintain the expandable member 16 in a collapsed or non-expanded position when the expandable member 16 is disposed in the outer member 14. Outer member 14 has an inner diameter or size to receive the inner member 12 while permitting relative movement of the inner member 12 and/or the outer member 14. Outer member 14 terminates distally at a distal end 34 and proximally at a knob or flange 36. Knob 36 can have any desired configuration to facilitate grasping thereof by the hand grasping hub 18 to move outer member 14 relative to inner member 12. As shown in FIG. 1, knob 36 has an enlarged annular configuration with ridges or grooves thereon to enhance grasping. Outer member 14 for the instrument 10 is slidably disposed on inner member 12 for movement between an extended position, shown in FIG. 1, wherein the expandable member 16 is disposed within the outer member 14 to be maintained in the non-expanded position and a retracted position, shown in FIG. 2, wherein the expandable member 16 is exposed for movement to the expanded position. It should be appreciated that various handle structure, other than the hub and knob shown, can be coupled with inner member 12 and with outer member 14 for moving the outer member 14 between the extended and retracted positions and that such handle structure can include various locking mechanisms for fixing the relative position of the inner and outer members. In instrument 10, the position of the outer member 14 relative to the inner member 12 is retained by friction.

The instrument 10 as described above is representative of the subject invention in basic form. However, it should be appreciated that various modifications and/or additions can be made to the subject invention as explained further below.

Figure 5:
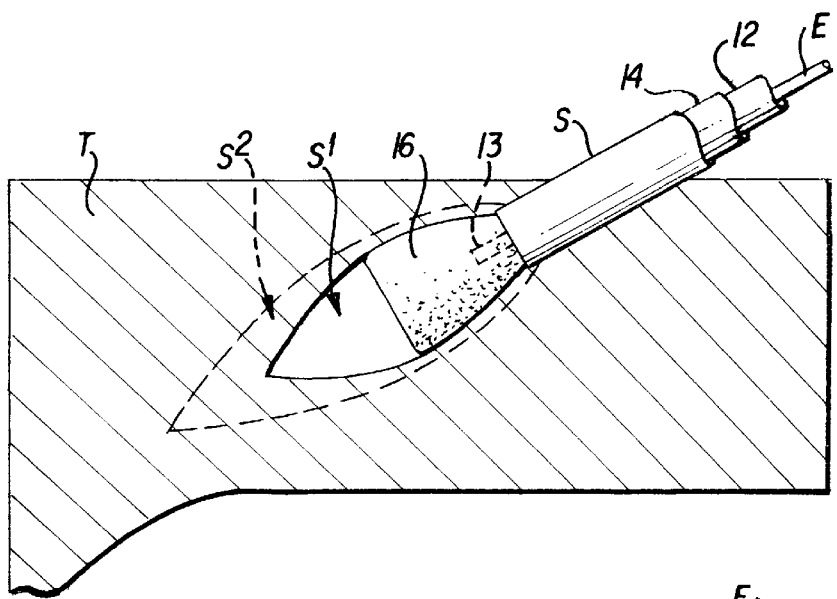
FIG. 5 is a broken perspective view of the expandable multifunctional instrument of FIG. 4 creating an initial space at the obstructed site.

In use, the instrument 10 is normally provided with the outer member 14 in the extended position such that the expandable member 16, which is normally provided in the non-expanded position is disposed within the outer member 14 as illustrated in FIG. 1. With the outer member 14 in the extended position, the outer member distal end 34 will be disposed distally of the inner member distal end 20 a distance that is at least as great as the length L of the portion of expandable member 16 that protrudes from inner member 12 such that no part of expandable member 16 is exposed during introduction in the body. With outer member 14 in the extended position and expandable member 16 in the non-expanded position, the instrument 10 is introduced at a potential space at an obstructed site in the body through an endoscopic portal, which can be a relatively small size natural or incisional opening or an instrument channel such as a portal or trocar sleeve. FIG. 4 illustrates the instrument 10 being introduced at a potential space at an obstructed anatomical site through the lumen of a portal or trocar sleeve S having a distal end positioned within the body, typically via a penetrating member disposed within the portal sleeve S and withdrawn therefrom upon positioning of the portal sleeve distal end at the desired location. The obstructed site shown in FIG. 4 is within homogenous tissue T and is obstructed in that there normally is no space in tissue T for visualization or for performing operative procedures. The distal end 34 of outer member 14 is positioned at the obstructed site; and, once the outer member distal end 34 is properly positioned at the potential space, knob 36 is manually moved proximally toward hub 18, as shown by the arrow in FIG. 4, to move outer member 14 proximally relative to inner member 12 to the retracted position. It should be appreciated that, depending on procedural use, the knob 36 and hub 18 can be grasped with a single hand such that inner member 12 and outer member 14 can both be moved relative to one another in a squeezing action to move the outer member 14 to the retracted position. FIG. 5 illustrates the outer member 14 in a fully retracted position wherein the outer member distal end 34 is disposed proximally of the expandable member distal end 24 a distance equal or substantially equal to length L such that the entire or substantially the entire portion of the expandable member 16 that protrudes beyond the inner member is exposed. However, it should be appreciated that the outer member 14 can be selectively, manually moved to various intermediate retracted positions between the extended position and the fully retracted position where it is desired to expose less of the expandable member. Prior to moving expandable member 16 from the non-expanded position to the expanded position, a visualizing instrument such as an endoscope E can be introduced in the lumen of inner member 12 via inlet tube 28 to position an image receiving distal end 13 of the endoscope E within the expandable member 16. Accordingly, the position of expandable member 16 at the obstructed site can be confirmed visually prior to creation of the operating space.

To create an operating space at the obstructed site utilizing the instrument 10, fluid is supplied to the interior of expandable member 16 through inlet tube 28 and the lumen of inner member 12 to move the expandable member 16 from the non-expanded position to the expanded position as illustrated in FIG. 5. By controlling fluid flow to and from expandable member 16, the size of expandable member 16 in the expanded position can selectively be made larger or smaller in accordance with the size of space desired to be created and depending on procedural use. Movement of expandable member 16 to the expanded position causes an initial space $S^1$ to be created at the obstructed site due to pushing, displacement, dilatation, dissection or retraction of tissue by expandable member 16. The initial space $S^1$ can be enlarged, if necessary, by moving the instrument 10, such as back and/or forth in a longitudinal direction as shown by the arrow in FIG. 5, to further retract, dissect, separate or move the tissue T to create a second space $S^2$ shown in dotted lines, and the initial and second spaces can be created under direct visualization by endoscope E.

Accordingly, the instrument 10 allows an actual operating space to be created from a potential space at an obstructed site for visualization and/or treatment of adjacent tissue and to permit various procedures to be performed utilizing the thusly created operating space. The present invention allows an operating space to be created with a two-step procedure whereby a small initial space is created at the obstructed site for visualization and, upon visual confirmation of proper location of the initial space, a second larger space is created from the initial space to provide the room needed to perform various operative procedures. By providing direct visualization via the initial space, connective tissue structure can be cut, if necessary, under direct visualization to permit separation of the tissue to create the second, final space. Additionally, if the initial space is improperly located, the proper location can be found without a larger final space already having been formed.

The instrument 10 can remain in place to maintain the operating space and/or to manipulate tissue. The instrument itself can define an operating or working space within the expandable member via which various procedures can be performed. Where the instrument remains in place, the instrument can be utilized to recreate the operating space in the event that the operating space collapses or is lost. The expandable member 16 can have a passage therethrough as explained further below to allow fluid and/or various additional instruments to be introduced at the operating space. Although instrument 10 is illustrated in conjunction with a single portal, it should be appreciated that additional portals can be placed in communication with the operating space for introduction of various instruments in multiple puncture procedures.

Subsequent to creation of initial space $S^1$, the second larger operating space $S^2$ can be created in various ways other than and/or in addition to moving the instrument 10. One way of creating space $S^2$ is by introducing insufflation fluid under pressure at the initial space $S^1$. Suitable fluids include $CO_2$, $N_2O$, distilled water, saline, high density glucose such as Hyscon, Dextran, transparent medical grade jelly or viscoelastics such as Hilan. The insufflation fluid can be introduced through sleeve S, endoscope E, instrument 10 where the instrument is provided with a passage or through a second portal in multiple puncture procedures. Another way to create space $S^2$ is by introducing another expandable multifunctional instrument at the initial space $S^1$ through the passage of instrument 10 or a second portal. Where the instrument 10 is withdrawn from sleeve S subsequent to creation of the operating space, the operating space can be maintained by introducing insufflation fluid, particularly Dextran or jelly, at the operating space.

The size and configuration of the space created with the expandable multifunctional instrument will depend on the size and configuration of the expandable member in the expanded position and on the nature of the anatomical tissue at the obstructed site. For example, in some cases the anatomical tissue will substantially conform to the expandable member in the expanded position such that a space corresponding substantially in size and shape to the expandable member will be formed, whereas in other cases a space larger in size than the expandable member will be formed due to separation of tissue layers. Depending on the nature of the tissue, the instrument can be moved from externally of the body to gently manipulate connective structure of the tissue to permit the tissue to be separated to facilitate creation of the operating space.

Various fluids can be utilized to move the expandable member between the non-expanded position and the expanded position including the various insufflation fluids described herein. Preferred substances include Dextran, high viscosity gels and other substances that are immiscible with blood such that visibility is not obscured in the event that the expandable member bursts in the body as it would be in the case of immiscible substances such as saline. Where all or part of the expandable member 16 is covered with the layer of absorbent material 22 or formed of absorbent material, the absorbent material can be utilized to absorb or collect bodily fluids, such as blood. The expandable member 16 and/or the absorbent material 22 can carry various coagulating, anticoagulating, antibiotic and therapeutic substances. The outer surface of expandable member 16 can be irregular or rough to contact and/or treat anatomical tissue depending on procedural use. Various visualizing devices, including endoscopes and charge coupled devices, can be utilized for visualization.

Figure 6:
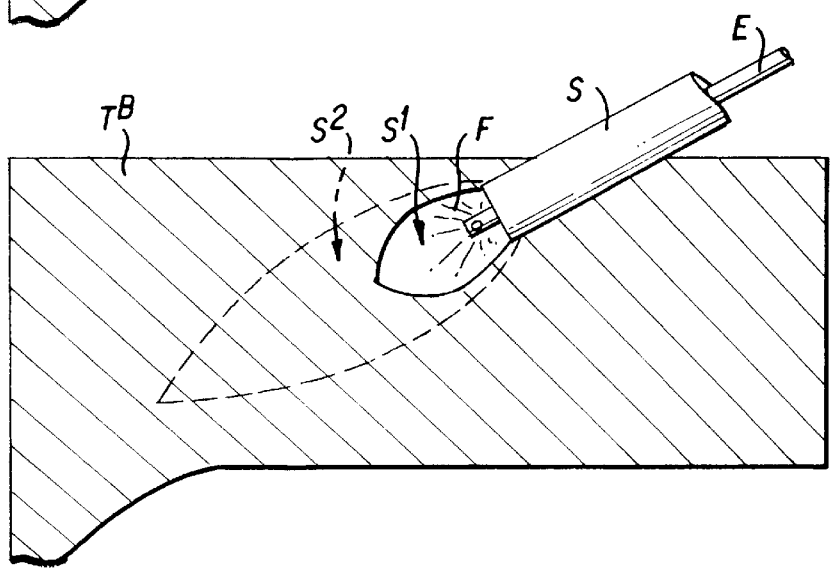
FIG. 6 is a broken perspective view illustrating another method of creating a space at an obstructed site in anatomical tissue showing fluid under pressure being introduced at the obstructed site.

In accordance with a modification of the method described above, insufflation fluid is introduced or injected at the obstructed site to create the initial space $S^1$ prior to introduction of the expandable multifunctional instrument or prior to movement of the expandable multifunctional instrument to the expanded position. The fluid can be introduced at the obstructed site through portal sleeve S, the expandable multifunctional instrument or through another instrument or portal communicating with the obstructed site. Many various instruments can be utilized to introduce or inject fluid under pressure at the obstructed site including needles, Tuohy needles, safety needles, Verres needles and standard and safety trocars with pressure syringes or pressure pumps with gauge indicators. FIG. 6 illustrates fluid F being introduced at an obstructed site within breast tissue $T^B$ through portal sleeve S to displace tissue $T^B$ to create initial space $S^1$. Creation of initial space $S^1$ in the desired location can be confirmed visually via endoscope E introduced through the portal sleeve S or through a second portal in multiple puncture techniques. To create the operating space $S^2$, the instrument 10 is introduced at the initial space $S^1$ through the portal sleeve S, through the instrument used to introduce fluid, through an additional portal communicating with initial space $S^1$ or through the endoscope E where the endoscope E has an operating channel. The expandable member 16 is exposed in or adjacent the initial space $S^1$ and is moved to the expanded position as described above to create operating space $S^2$. The method of creating spaces at an obstructed site by introducing fluid at the obstructed site is particularly useful in organ structures and procedures including the breast, lungs, brain, structure adjacent embolic or anuretic arteries or veins, retroperitoneal spaces, various layers of the spinal cord, preperitoneal spaces for ventral hernia or inguinal hernia repair, subcutaneous tissue such as procedures involving the removal of ganglia, benign lumps or melanoma, bowel or bowel wall, liver, spleen, pancreas, kidney, gall bladder, uterine wall, the space of Retzius utilizing liquid injection or introduction, pathological locations and locations adjacent pathological locations.

Some of the various modifications that the expandable multifunctional instrument 10 can have include a spine 40 and a directional control system 42. Spine 40, as illustrated in FIG. 2, can be disposed inside of expandable member 16, within the material forming expandable member 16 or outside of expandable member 16 for shaping, rigidifying and/or expanding the expandable member 16. Spine 40 is disposed within expandable member 16 and includes a plurality of arms 44 having proximal ends connected to the distal end of inner member 12 and distal ends joined to inwardly bent or angled fingers 46. Fingers 46 are bent or angled from arms 44 in the direction of a longitudinal axis of instrument 10 to terminate at rounded nubs 47 forming a smooth profile or surface configuration for expandable member 16. Spine 40 has a preformed triangular configuration in side view with arms 44 biased outwardly in a direction away from the instrument longitudinal axis to bias the expandable member 16 to the expanded position, and the spine has a flat configuration in end view with arms 44 aligned with one another. Arms 44 are movable inwardly in the direction of the longitudinal axis of instrument 10 to permit expandable member 16 to be moved to the non-expanded position. Various materials including various spring materials, such as metals or plastics can be utilized for spine 40 and it is desired that the spine 40 have sufficient rigidity to maintain the shape of expandable member 16 in the expanded position and to permit manipulation of anatomical tissue.

Figure 7:
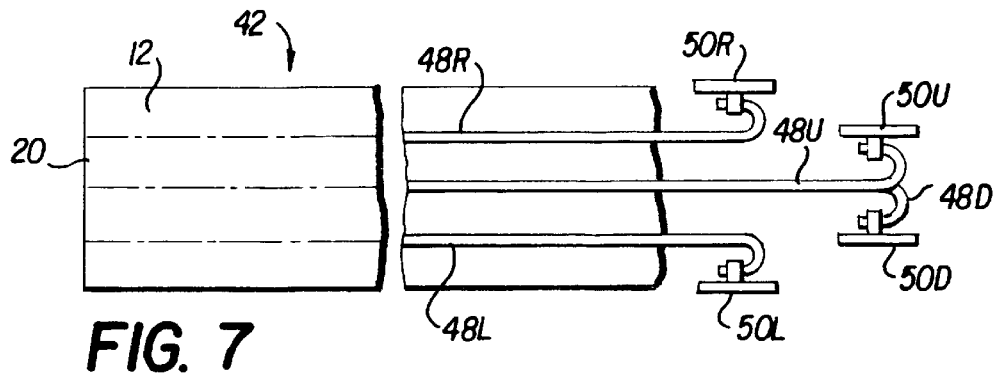
FIG. 7 is a schematic view of a directional control system for the expandable multifunctional instrument of FIG. 1.

The directional control system 42 is illustrated in FIG. 2 and schematically in FIG. 7. The directional control system 42 is for use with a flexible or partly flexible or bendable inner member having at least a flexible distal end portion. The directional control system 42 includes left and right control wires 48L and 48R and up and down control wires 48U and 48D extending longitudinally along inner member 12 and having distal ends connected with the inner member distal end 20 and proximal ends connected with left and right control wheels 50L and 50R and up and down control wheels 50U and 50D, respectively, mounted on hub 18, only the left control wheel 50L being shown in FIGS. 1 and 2. Winding of one or more of the control wires 48 via rotation of the corresponding control wheels 50 causes corresponding selective angular movement or bending of the inner member distal end and unwinding of the control wires via rotation of the control wheels causes the inner member to be straightened as disclosed in prior application Ser. No. 08/249,116.

Figure 8:
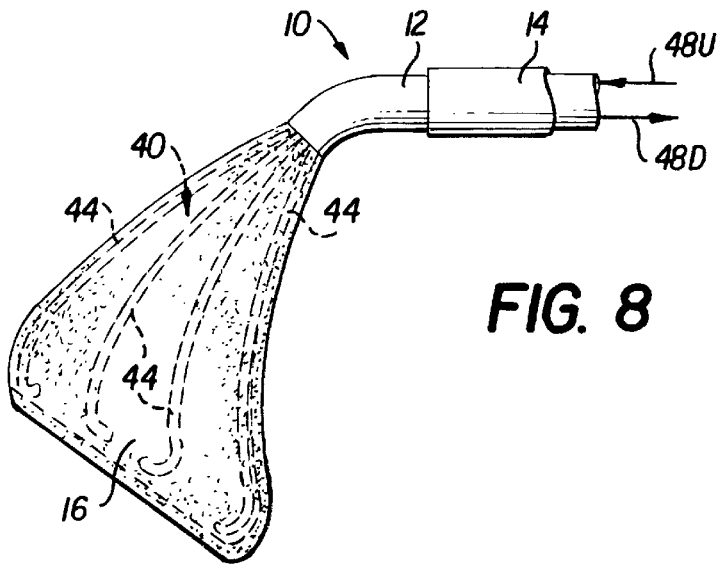
FIG. 8 is a broken perspective view of the expandable multifunctional instrument of FIG. 1 illustrating use of the directional control system to adjust the angular orientation of the expandable member.

Use of instrument 10 having spine 40 and directional control system 42 is similar to that described above except that expandable member 16 is maintained in the non-expanded position via constraint of spine 40 by outer member 14 in the extended position. Movement of outer member 14 to the retracted position releases arms 44 to automatically spring outwardly to move expandable member 16 to the expanded position to create an initial space at an obstructed site with the spine 40 maintaining and/or rigidifying the expandable member in the expanded position. Spine 40 can be utilized to move the expandable member to the expanded position mechanically, with or without fluidic expansion of the expandable member; however, in instrument 10 fluid can be supplied to the expandable member 16 as described above to fill out the configuration of the expandable member or to further expand the expandable member 16 to increase the size of the expandable member in the expanded position. In order to change the direction or orientation of expandable member 16, one or more of the control wheels 50 are rotated to move the corresponding control wires 48 to change or adjust the angular orientation of expandable member 16. For example, FIG. 8 illustrates the instrument 10 subsequent to angular adjustment wherein a longitudinal axis of expandable member 16 is angularly offset from the longitudinal axis of instrument 10. As shown in FIG. 8 the outer member 14 in the retracted position is moved proximally a distance sufficient to expose the flexible inner member distal end portion. Alternatively, at least the distal end portion of the outer member 14 can be made flexible or bendable such that the outer member distal end 34 can be aligned or substantially aligned with the inner member distal end 20 in the retracted position while permitting angular adjustment. FIG. 8 illustrates the up control wire 48U extended or advanced in the direction of the corresponding arrow and the down control wire 48D wound or retracted in the direction of the corresponding arrow to move the inner member distal end portion angularly downwardly, and the control wires can be utilized to articulate the expandable member angularly. It should be appreciated that angular movement of the expandable member can be utilized to create a space at the obstructed site by retracting or manipulating tissue. Instrument 10 having spine 40 is withdrawable from the body subsequent to release of fluid from expandable member 16 and/or movement of outer member 14 to the extended position to constrain spine 40.

Various spines can be utilized in the expandable multifunctional instruments of the present invention, and the spines can be designed in many various ways to have various diverse predetermined configurations in the expanded position including flat and non-flat configurations. The spines can be designed as multiple articulating pivotable or jointed arms as disclosed in the prior applications. The spines can be attached to various components other than the inner member or the spines can themselves be separate, independent components as described further below. The spines can be hollow or tubular to permit inflation of the expandable members through the spines, and the spines can be used for irrigation, aspiration or drainage and/or for supplying medicaments. The spines can be utilized to rigidify the expandable members for use in manipulating organ or tissue structure.

The expandable multifunctional instruments can be designed in many various ways to provide the expandable members to be normally disposed at an angle with the instrument longitudinal axes. For example, instead of the directional control system, any one or more of the inner member, the outer member or the spine can include a resilient, flexible, bendable or deformable segment or neck having a predetermined bend, curve, angle or shape memory to normally position or bias the expandable member to a position where the longitudinal axis of the expandable member is offset from the longitudinal axis of the instrument as described in prior application Ser. No. 08/249,116. One way of forming the segment or neck is as a spring segment, such as a length of coiled wire, having a predetermined bias or shape memory.

FIG. 9 illustrates at 110 a modification of an expandable multifunctional instrument according to the present invention having a hollow spine 140. Expandable multifunctional instrument 110 includes tubular inner member 112, outer member 114 and expandable member 116. Expandable member 116 has an open distal end 124 connected to the distal end 120 of inner member 112 at a circumferential seal and an open proximal end connected at a circumferential seal to a cylindrical, double-walled body 156 of spine 140. Inner member 112 is disposed within the cylindrical body 156 and protrudes distally therefrom such that the inner member 112 forms a central working or operating channel through expandable member 116 for introduction of fluids and/or instruments. Spine 140 includes tubular or hollow arms 144 connected with body 156, which has an inner circumferential wall 158 and an outer circumferential wall 160 spaced from inner wall 158 to define a passage 162 therebetween communicating with the interiors of arms 144. Arms 144 are disposed within expandable member 116 with holes or apertures 164 in arms 144 providing fluid communication between passage 162 and the interior of expandable member 116. Inner member 112 extends entirely through hub 118, which has a truncated conical or triangular profile in side view, to terminate at valve 132 controlling opening and closing of the inner member lumen. Body 156 extends into hub 118, and supplemental inlet ports, conduits or passages 180 extend transversely through hub 118 to communicate with passage 162. Valves 182 are mounted externally along hub 118 or within recesses of hub 118 for selectively controlling fluid flow through supplemental inlet conduits 180 and, therefore, through spine 140.

Outer member 114 terminates proximally at a transverse flange 166 having an external thread 168 thereon. Knob 136 for instrument 110 has an elongate, distally tapered configuration with a cylindrical internal passage 170 defined by an inner cylindrical wall having a thread 172 thereon. Flange 166 is disposed in passage 170 with thread 168 in cooperative engagement with thread 172. Body 156 extends entirely through the passage 170 and has a transverse flange 176 mounted in a recess in an end wall of knob 136 to permit rotation of knob 136 relative to the spine 140.

Operation of instrument 110 is similar to that described for instrument 10 except that the outer member 114 is moved relative to the inner member 112 between the extended and retracted positions by manually rotating knob 136. FIG. 9 illustrates flange 166 in dotted lines at a distal end of passage 170 at which time the outer member 114 is in the extended position. Rotation of knob 136 in a first direction of rotation will cause flange 166, via threads 168 and 172, to be moved proximally along passage 170 causing corresponding proximal movement of outer member 114 relative to inner member 112 from the extended position to the retracted position shown in FIG. 9. Movement of outer member 114 to the retracted position causes arms 144 to spring outwardly to move the expandable member 116 from the non-expanded position to the expanded position. The expandable member 116 can be maintained in the expanded position or moved to a further expanded position via inflation through spine 140 in that supplemental inlet ports 180 can be utilized to supply fluid to the interior of expandable member 116 via passage 162, arms 144 and holes 164. Various instruments or fluids can be introduced through the operating or working channel defined by the inner member 112. The instrument 110 can include a penetrating member disposed in the inner member 112 for penetrating anatomical tissue to introduce expandable member 116 at the obstructed site. Knob 136 is rotated in a second direction of rotation to cause flange 166 and, therefore, outer member 114, to be moved distally toward the extended position causing movement of expandable member to the non-expanded position by constraint of spring 140 for withdrawal of instrument 110 from the body.

Figure 10:
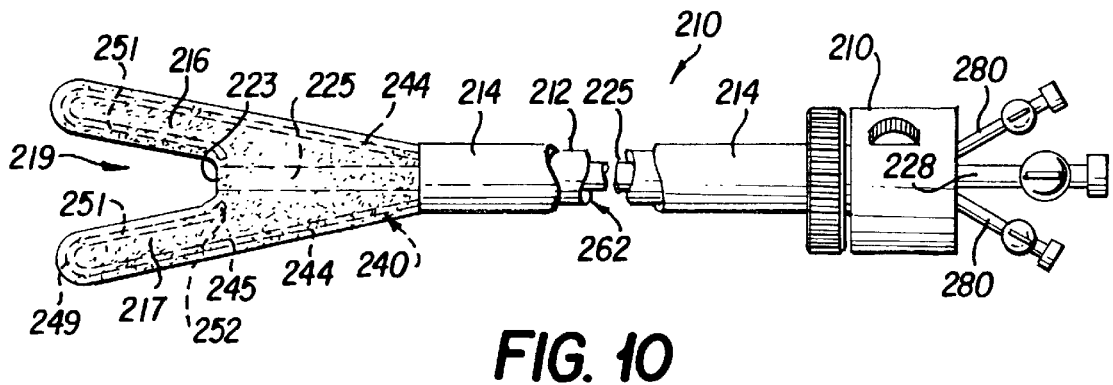
FIG. 10 is a broken side view of another modification of an expandable multifunctional instrument according to the present invention having an expandable member defining a multiple finger shape.

FIGS. 10–13 illustrate various modifications of expandable multifunctional instruments wherein the expandable members have multiple finger shapes particularly advantageous for holding, retracting or manipulating tissue or organ structure. FIG. 10 illustrates an expandable multifunctional instrument 210 having a generally V-shaped expandable member 216 defining two outwardly angled fingers 217 with a space or opening 219 between fingers 217 for receiving tissue or organ structure. Expandable member 216 has a proximal end disposed over and connected to the distal end of inner member 212 and a recessed end portion connected to a distal end 223 of a control tube 225 disposed concentrically within inner member 212. The proximal end of inner member 212 and a proximal end of control tube 225 are mounted to a hub 218 to position the distal end 223 of the control tube distally of the distal end of inner member 212 such that the control tube 225 defines an operating or working channel through expandable member 216 communicating with or formed integrally with inlet tube 228. The outer diameter of control tube 225 is slightly smaller than the inner diameter of inner member 212 to define a minimal gap or space 262 therebetween to permit fluid flow between the inner member 212 and the control tube 225. The proximal ends of inner member 212 and control tube 225 extend into hub 218, and supplemental inlet ports 280 extend through hub 218 and the wall of inner member 212 to communicate with the gap 262 between inner member 212 and the control tube 225 for supplying fluid to the interior of expandable member 216.

A spine 240 for instrument 210 includes a pair of arms 244 having proximal ends connected to the distal end of inner member 212. Arms 244 each include a first straight segment 245 extending distally beyond the distal end 223 of control tube 225 to extend into a finger 217 and a curved or U-shaped segment 249 defining a tip of finger 217 and joining a distal end of the first straight segment 245 to the distal end of a second straight segment 251 extending proximally from the curved segment 249 toward the distal end 223 of control tube 225 to terminate at a gently curved or angled end portion 252 at the base of fingers 217. The first and second straight segments 245 and 251 are parallel or substantially parallel to one another to define a width for fingers 217 with the first straight segments defining an outer edge and the second straight segments defining an inner edge for fingers 217. Spine 240 biases expandable member 216 to the expanded position shown in FIG. 10 in that arms 244 are biased angularly outwardly in a direction away from the instrument longitudinal axis to bias fingers 217 angularly outwardly. When the expandable member 216 is disposed within the outer member 214 with the outer member in the extended position, the expandable member 216 will be moved to the non-expanded position due to collapse or constraint of spine 240 by the outer member 214. Movement of the outer member 214 from the extended position to the retracted position causes arms 244 to spring outwardly thusly moving expandable member 216 to the expanded position automatically, and fluid can be supplied to the expandable member 216 through supplemental inlet ports 280 and the gap 262 between the inner member 212 and the control tube 225.

A modification of an expandable multifunctional instrument according to the present invention is illustrated in FIG. 11 at 310 wherein only a distal portion of the instrument 310 is shown. Instrument 310 includes expandable member 316 defining three distally protruding fingers with spaces 319 between the fingers. Expandable member 316 is provided without a control or operating channel and includes a central or inner finger 317' aligned or substantially aligned with a longitudinal axis of instrument 310 and two lateral or outer fingers 317" angularly disposed on opposite sides of central finger 317'. Spine 340 for instrument 310 includes a central or inner U-shaped arm 344' and two lateral or outer arms 344" coupled with inner member 312. Arm 344' has parallel first and second straight segments 345' and 351' extending distally into finger 317' to terminate at a curved segment 349' joining the straight segments 345' and 351' and defining a tip of finger 317'. Arms 344", which are similar to arms 244, each include a first straight segment 345" extending distally into a finger 317" and a curved segment 349" joining a distal end of the first straight segment 345" to the distal end of a proximally extending second straight segment 351" terminating at curved end portion 352" adjacent inner arm 344' at the base of fingers 317". Arms 344" are biased angularly outwardly in a direction away from a longitudinal axis of instrument 310 to bias expandable member 316 to the expanded position when outer member 314 is moved to the retracted position as shown in FIG. 11.

FIG. 12 illustrates a distal portion of an instrument 410 including expandable member 416 defining four fingers, two inner fingers 417' and two outer fingers 417" with spaces 419 between the fingers. Instrument 410 includes a spine 440 having two arms 444 joined to a body 456 disposed in inner member 412. Each arm 444 includes a straight segment 445" extending distally into an outer finger 417", a first U-shaped segment 449" joined to straight segment 445" and defining a tip of outer finger 417" and a second U-shaped segment 449' defining a tip of an inner finger 417' and connected to the first U-shaped segment by a curved segment 453'. The second U-shaped segments 449' terminate at curved end portions 452' adjacent one another at the base of inner fingers 417' to provide continuity and smoothness. Arms 444 are biased angularly outwardly in a direction away from a longitudinal axis of instrument 410 to move the expandable member 416 to an expanded position automatically when the outer member 414 is in the retracted position as shown in FIG. 12.

FIG. 13 illustrates a distal portion of an instrument 510 including an expandable member 516 defining five fingers with spaces 519 therebetween. The fingers defined by expandable member 516 include two outer fingers 517" and three inner fingers 517'. A spine 540 for instrument 510 includes five arms 544, one for each finger. Arms 544 each include first straight segments 545 extending distally into the fingers, U-shaped segments 549 defining tips for the fingers and joining the first straight segments to proximally extending second straight segments 551 terminating at curved end portions 552 at the base of the fingers with the exception of outer arm 544" which has a second straight segment 551" extending proximally along an outer side edge of expandable member 516 to terminate at inner member 512. Arms 544 have a predetermined bias or shape memory to move the expandable member 516 to the expanded position shown in FIG. 13 wherein the expandable member assumes an open, hand-like configuration when the outer member 514 is moved to the retracted position. Inner member 512 for instrument 510 has a distal end portion 543 formed with a predetermined bend or angle to angularly position the expandable member 516 automatically in response to movement of the outer member 514 to the retracted position.

FIG. 14 illustrates a distal portion of an expandable multifunctional instrument 610 including an elongate cylindrical expandable member 616 having an elongate spine 640 therein normally assuming a curved J-shaped configuration when outer member 614 is in the retracted position as shown. Spine 640 is moved to a substantially straight configuration by the outer member 614 when the outer member is moved to the extended position. It should be appreciated that the spines for the multiple finger-shaped expandable members described in FIGS. 10–13 above can have a predetermined curve or J-shape as described for spine 640 to produce various curved multiple finger shapes. In particular, an expandable member having a curved, hand-like configuration is particularly useful for pulling the appendix out from the retroperitoneal space.

The multiple finger shapes illustrated in FIGS. 10–13, particularly when curved, are advantageous for grabbing tissue and, in particular, for pulling tissue aside and holding the tissue out of the way to create a space for operative procedures and for use in exposure and dissection. The fingers can be individually controllably bent, angled or curved with the use of various directional adjustment means.

FIG. 15 illustrates at 716 a modification of an expandable member wherein the expandable member 716 is mechanically expanded via a spine 740 constructed as a fan-like spring plate. Spine 740 includes a plurality of flat arms 744 having proximal ends pivotally connected to one another in overlapping fashion at a joint 754. Joint 754 includes a spring (not shown) rotationally biasing the arms 744 to assume an open fan-like configuration to move the expandable member 716 to the expanded position as shown. The expandable member 3716 is particularly useful for creating an operating space to access lumps between adjacent organs.

Another modification of an expandable multifunctional instrument according to the present invention is illustrated in FIG. 16 at 810. Expandable multifunctional instrument 810 includes expandable member 816 having a C-shaped configuration in the expanded position and formed of two semi-circular expandable member portions 816a and 816b. Portions 816a and 816b have tapered distal ends 824a and 824b separated by a space 819 communicating with a central operating or working space 827 defined by the expandable member portions 816a and 816b such that the space 827 is disposed within or circumscribed by the expandable member. Expandable member portions 816a and 816b have closed distal ends and proximal ends 826a and 826b secured to body portions 856a and 856b, respectively, of spine 840 to form two fluid-tight envelopes. Body portions 856a and 856b are disposed in inner member 812 and are tubular or hollow. Body portions 856a and 856b extend longitudinally through inner member 812 to terminate proximally in hub 818 in communication with supplemental inlet ports 880a and 880b, respectively. Body portions 856a and 856b are distally joined to hollow, semi-circular arms 844a and 844b, respectively, curving outwardly in a direction away from a longitudinal axis of the instrument 810. Arms 844a and 844b have inwardly, proximally curving distal end portions 829a and 829b, respectively, forming a smooth contour at opening 819 with rounded protuberances 831a and 831b extending into the tapered distal ends of the expandable member portions. Arms 844a and 844b communicate with the lumens of body portions 856a and 856b, respectively, and holes 864 are provided in arms 844a and 844b to permit fluid to be supplied to the interior of expandable member portions 816a and 816b. Hub 818 has a cylindrical configuration with an inlet tube 828 communicating with the lumen of inner member 812 and supplemental inlet ports 880A and 880B, respectively angularly disposed on opposite sides of inlet tube 828. The proximal ends of inner member 812 and spine 840 are mounted to hub 818 to position body portions 856a and 856b within inner member 812 and arms 844a and 844b within expandable member portions 816a and 816b, respectively. The outer member 814 for instrument 810 has indicia 833 thereon for providing a visual indication of the depth of insertion of the outer member 814 in the body.

Use of instrument 810 is similar to that previously described in that arms 844a and 844b normally assume a semi-circular configuration to shape or move the expandable member portions 816a and 816b, respectively, to the expanded position when the outer member, 814 is retracted as shown. Fluid can be supplied to one or both of the expandable member portions 816a and 816b through spine 840 and supplemental inlet conduits 880a and 880b. The lumen of inner member 812 defines an operating channel allowing fluids and/or various instruments to be introduced at space 827 whereby operative procedures can be performed within the space 827. The flexibility of spine 840 allows the expandable member portions 816a and 816b to be moved toward or away from one another during use in response to contact by tissue or other instruments to change the size of operating space 827 for adjustability.

FIG. 17 illustrates at 910 the distal portion of a modification of an expandable multifunctional instrument wherein the expandable member 916 has a closed annular, ring, toroid or doughnut-shaped configuration. Expandable member 916 includes an outer wall 935 and an inner wall 937 secured to tubular body portions 956a and 956b of spine 940 to form a closed or sealed annular envelope or bag. Inner wall 937 has a passage defining portion 938 aligned with the lumen of inner member 912 to define an operating or working channel communicating with operating space 927. The outer and inner walls 935 and 937 are continuous at the distal end of expandable member 916 to form a closed circular or oval shape. Spine 940, which is similar to spine 840, includes body portions 956a and 956b disposed in inner member 912 and connected with semi-circular or curved arms 944a and 944b extending into expandable member 916. Arms 944a and 944b are hollow or tubular to communicate with the lumens of body portions 956a and 956b, respectively, and holes 964 in arms 944a and 944b allow fluid to be supplied to the interior of expandable member 916 via supplemental inlet ports communicating with body portions 956a and 956b. Various instruments and/or fluids can be introduced at the operating space 927 through the lumen of inner member 912 and the passage defining portion 938 of expandable member 916. Arms 944a and 944b normally assume an outwardly curving configuration to move or shape the expandable member 916 to the expanded position when the outer member 914 is moved to the retracted position as shown.

Figure 18:
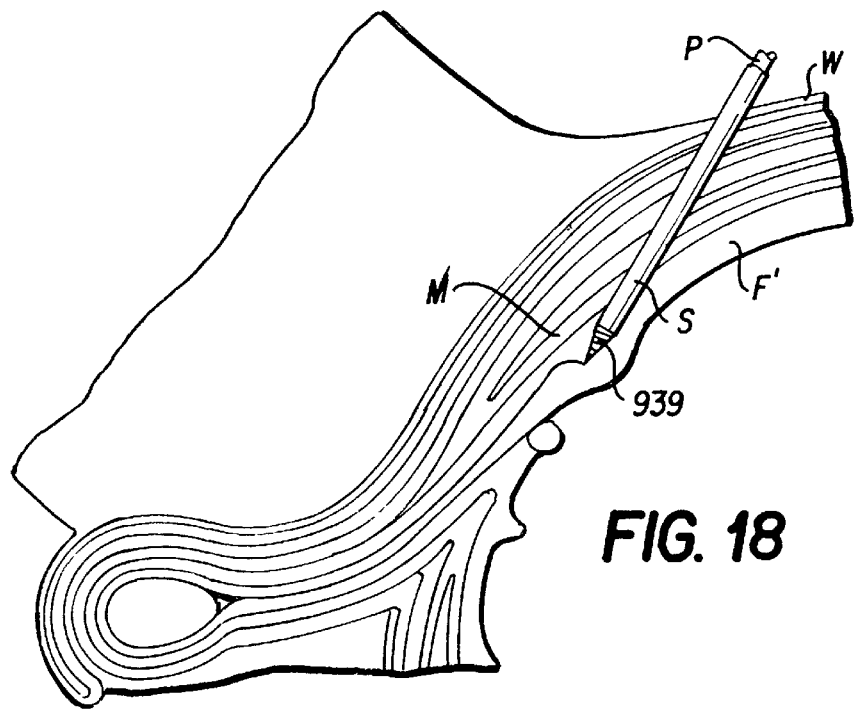
FIG. 18 is a broken perspective view illustrating a portal sleeve being introduced at an obstructed site in an anatomical wall.
Figure 19:
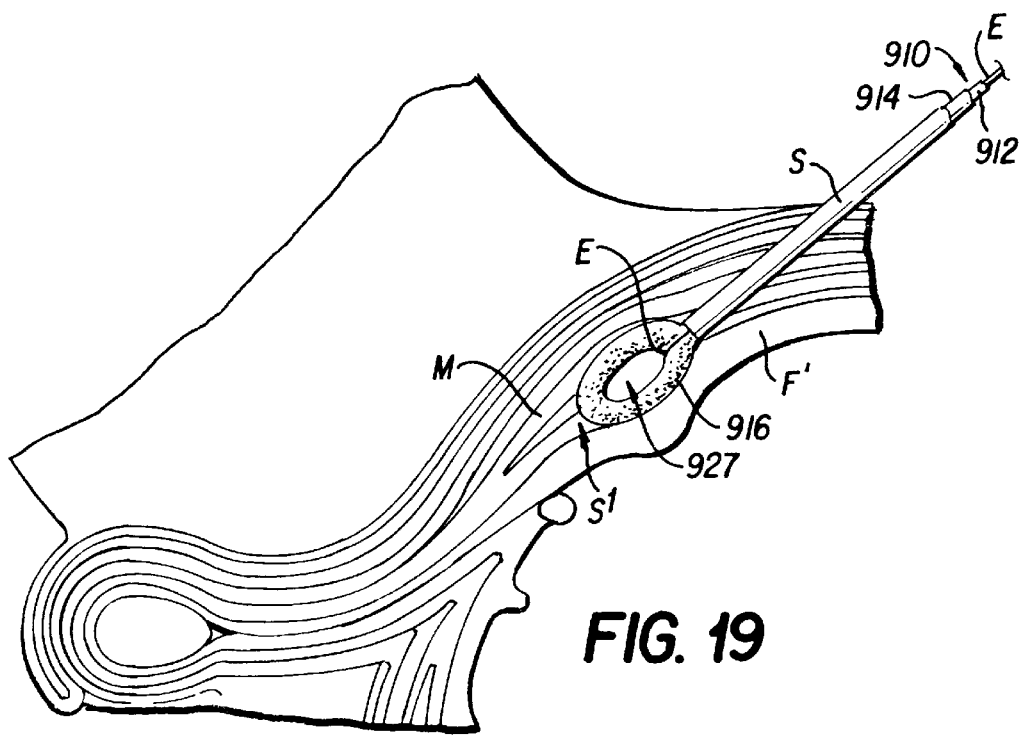
FIG. 19 is a broken perspective view illustrating the expandable multifunctional instrument of FIG. 17 introduced through the portal sleeve of FIG. 18 to create an initial space at the obstructed site.

FIGS. 18 and 19 illustrate use of instrument 910 to create an operating space at an obstructed site within an anatomical wall, such as wall W of the inguinal region which is obstructed due to the lack of space between adjacent layers of tissue forming wall W. As shown in FIG. 18, a penetrating instrument including a portal or trocar sleeve S and a penetrating member P, such as a trocar, disposed within the portal sleeve S is inserted into wall W. Penetrating member P has an externally threaded distal tip 939, which can be sharp or blunt, for controlled penetration into the anatomical wall W via rotation of the penetrating member P. The penetrating member P is inserted into the wall W to position a distal end of the portal sleeve S at an obstructed site in accordance with procedural use, and the threaded tip of the penetrating member allows the portal sleeve to be placed at the exact location or layer desired with reduced force. FIG. 18 illustrates the distal end of sleeve S positioned between the transverse abdominal muscle M and the layer of preperitoneal fat F'. Once the distal end of portal sleeve S has been properly positioned, the penetrating member P is withdrawn from the portal sleeve S leaving the portal sleeve S in place. Expandable multifunctional instrument 910 is then introduced through the portal sleeve S with the outer member 914 in the extended position such that the expandable member 916 is maintained in the non-expanded position. Once the instrument 910 is properly positioned at the obstructed site, the outer member 914 is moved to the retracted position to expose the expandable member 916. Arms 944a and 944b of spine 940 automatically spring outwardly to move the expandable member 916 to the expanded position causing separation of adjacent layers of wall W to create an initial space $S^1$ between the layer of muscle M and layer of fat F' as illustrated in FIG. 19. Fluid can be supplied to expandable member 916 to maintain or fill out the shape of the expandable member or to move the expandable member to a further expanded position to create a second larger space; however, the second larger space can also be created in the various ways previously described herein. A visualizing device, such as endoscope E, can be introduced through the lumen of inner member 912 and the passage defining portion of expandable member 916 to visually confirm proper space creation. The thusly created operating space can be utilized to conduct various operative procedures, and various operative procedures can be conducted within the operating space 927 of expandable member 916 under direct visualization by endoscope E. Various other instruments and/or fluids can be introduced through the inner member 912 and the passage defining portion 938 of the expandable member 916 or through the endoscope E. Accordingly, with the present invention, layers between the skin and peritoneum can be separated or dissected to create an operating space for performing operative procedures without entry into the peritoneum.

Various additional modifications of expandable multifunctional instruments having expandable members defining an operating or working space are illustrated in FIGS. 20–22 wherein only distal portions of the instruments are shown. The expandable member 1016 for the instrument 1010 shown in FIG. 20 has a triangular configuration in side view circumscribing a central triangular operating space 1027. The expandable member 1016 is provided with a spine 1040 including two outer arms 1044" extending along the outer lateral sides of expandable member 1016 and two inner arms 1044' extending along the sides of operating space 1027. Arms 1044' and 10441 are similar to arms 44 except that inner arms 1044' have intermediate shaped segments 1047 conforming in shape to the lateral sides of triangular operating space 1027. Inner member 1012 and outer member 1014 for instrument 1010 have flexible distal end portions and control wires 1048U and 1048D for changing the angular orientation of or for angularly articulating the expandable member 1016 via selective controlled bending and straightening of the inner and outer members.

The instrument 1110 illustrated in FIG. 21 is similar to instrument 1010 except that the expandable member 1116 defines a round operating space 1127. Spine 1140 for instrument 1110 is similar to spine 1040 except that the inner arms 1144' have curved intermediate segments 1147 conforming in shape to the lateral sides of operating space 1127. Inner member 1112 for instrument 1110 has a distal end portion 1143 formed of coiled wire having a predetermined bend. The distal end portion 1143 is held in a straight or substantially straight condition by the outer member 1114 in an extended position and automatically returns to the predetermined bent configuration when the outer member 1114 is moved proximally of the distal end portion 1143 in a retracted position as shown such that the angular direction of expandable member 1116 is adjusted automatically in response to retraction of the outer member 1114.

The instrument 1210 shown in FIG. 22 includes expandable member 1216 that is similar to expandable member 916 except that expandable member 1216 has a cylindrical configuration of increased depth or thickness. Spine 1240 for expandable member 1216 is similar to spine 940 except that spine 1240 has a plurality of arms 1244a and 1244b aligned with one another along the depth or thickness of expandable member 1216 and extending perpendicularly from branches 1255.

Figure 24:
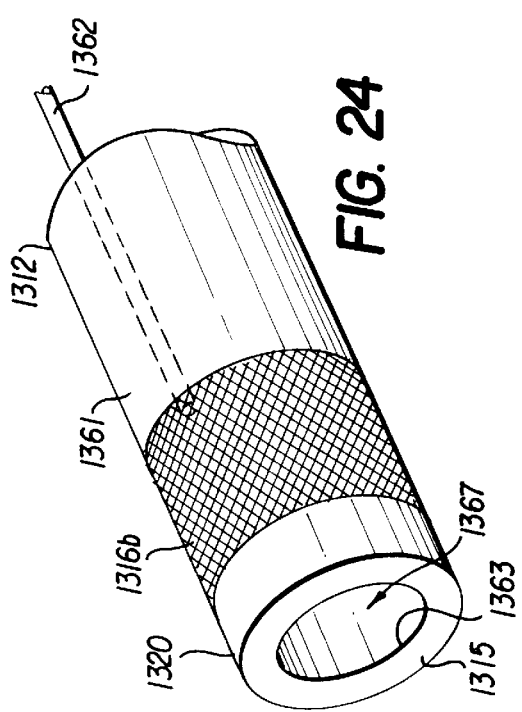
FIG. 24 is a broken perspective view of the inner member for the expandable multifunctional instrument of FIG. 23.

A modification of an expandable multifunctional instrument having multiple expandable members carried by relatively movable inner and outer members is illustrated at 1310 in FIG. 23. Instrument 1310 includes outer member 1314 carrying expandable member 1316a, inner member 1312 disposed within outer member 1314 and carrying expandable member 1316b and a penetrating member P disposed within inner member 1312. Inner member 1312 terminates distally at a distal end 1320 and proximally at a proximal end mounted to hub 1318. Outer member 1314 terminates distally at a distal end 1334 and proximally at a proximal end mounted to hub 1318. The outer member 1314 carries a threaded flange in cooperative engagement with a threaded internal cylindrical wall of knob 1336 allowing the outer member 1314 to be moved longitudinally relative to inner member 1312 as described previously for outer member 114. Penetrating member P can have various configurations according to procedural use including various solid, hollow and needle configurations. Penetrating member P has an externally threaded distal tip 1339 for penetrating anatomical tissue and a proximal end mounted to an end portion 1357 of hub 1318. The tip of penetrating member P can be sharp or blunt and, in the case of instrument 1310, the tip 1339 is somewhat blunt for particularly advantageous use in pleural and pericardial procedures. Hub 1318 includes a body portion 1359 mounting the proximal ends of inner member 1312 and outer member 1314 and end portion 1357 mounting the proximal end of penetrating member P with the end portion being removably secured to the body portion such as with the use of any suitable releasable detent allowing the penetrating member P to be withdrawn from the inner member 1312. Body portion 1359 includes a valve assembly, which can be conventional, for closing off or sealing the longitudinal passage through body portion 1359 when the penetrating member P is withdrawn from the inner member 1312. The expandable members 1316a and 1316b are carried adjacent the distal ends of outer member 1314 and inner member 1312, respectively, and are formed as outer wall portions of the outer member 1314 and the inner member 1312, which are of double-wall construction. FIG. 24 illustrates the construction of inner member 1312 which is also illustrative of the construction of outer member 1314. As shown in FIG. 24, the inner member 1312 is of hollow, double-wall construction having an outer wall 1361 and an inner wall 1363 joined by a transverse distal wall 1365 at inner member distal end 1320. The inner wall 1363 defines a lumen or passage 1367 through the inner member 1312 serving as an operating or working channel for the passage of fluid and/or instruments. Expandable member 1316b includes a layer of stretchable, elastic material forming a circumferential portion of outer wall 1361. A tube 1362 defining a fluid passage is disposed between outer wall 1361 and inner wall 1363 to couple expandable member 1316b with a supplemental inlet port 1380b disposed in hub body portion 1359. The construction of outer member 1314 is similar to that described for inner member 1312 with the fluid passage for the outer member coupling expandable member 1316a with a supplemental inlet port 1380a disposed in hub body portion 1359. An additional supplemental inlet port 1380c is disposed in hub body portion 1359 for supplying fluid through the lumen of inner member 1312.

It should be appreciated that the inner member 1312 and outer member 1314 can be designed or constructed in many various ways to couple the expandable members 1316 with the supplemental inlet ports and that the supplemental inlet ports can be disposed at various locations on the instrument 1310 in addition to the hub body portion as shown. For example, the space between the outer wall 1361 and the inner wall 1363 can be used as the fluid passage without a separate tube, the inner and outer members can be of solid wall construction with the tube or passage disposed in or formed by a channel drilled into the thickness of the solid wall or within a recess formed in the solid wall. The fluid passages 1362 and the supplemental inlet ports 1380 can be designed in many various ways and can include various structure for establishing fluid communication with the expandable members.

Figure 25:
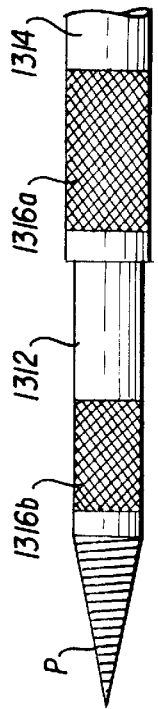
FIG. 25 is a broken side view of the expandable multifunctional instrument of FIG. 23 illustrating the outer member in a retracted position.
Figure 26:
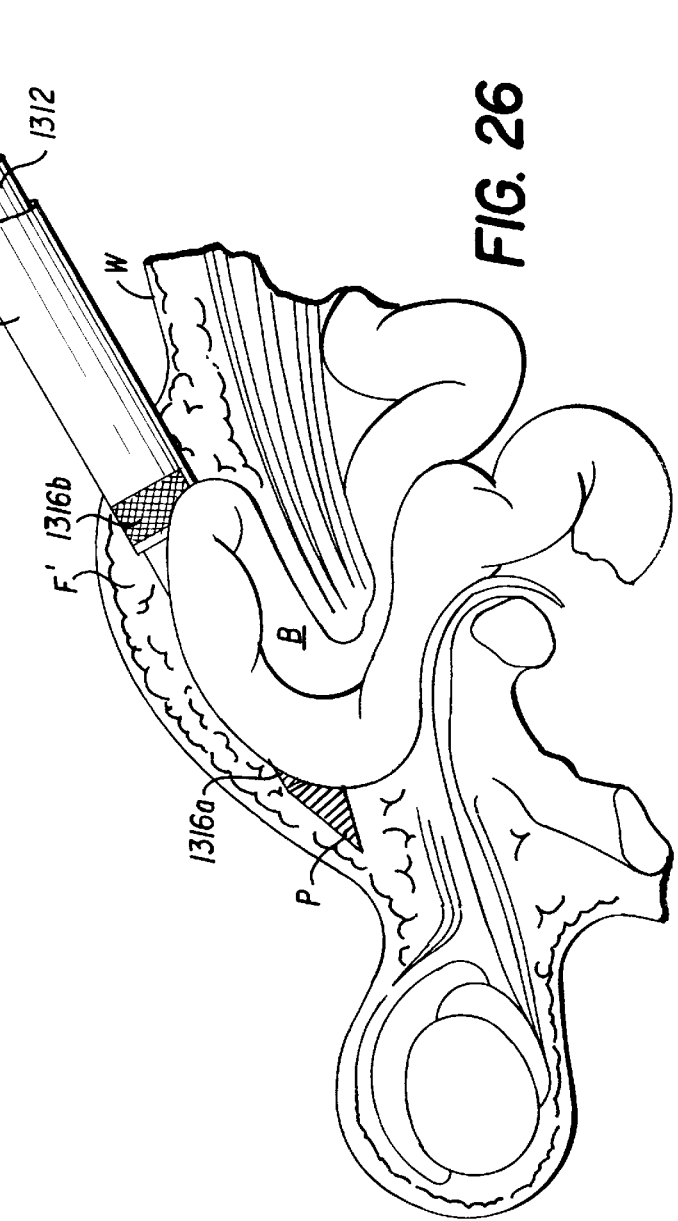
FIG. 26 is a broken perspective view illustrating the expandable multifunctional instrument of FIG. 23 introduced at an obstructed site in an anatomical wall.
Figure 27:
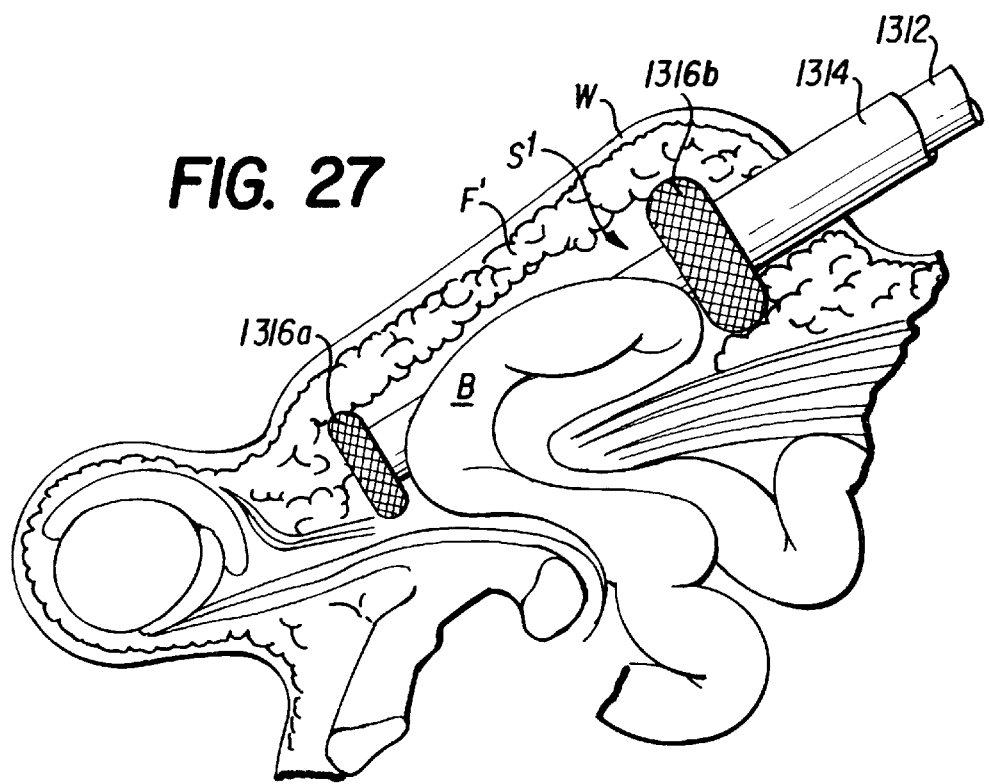
FIG. 27 is a broken perspective view illustrating the expandable members of the expandable multifunctional instrument of FIG. 26 in an expanded position to create an initial space at the obstructed site.

The inner member 1312 and the outer member 1314 are mounted to hub 1318 to normally position the outer member 1314 in an extended position wherein expandable member 1316a is disposed proximally of expandable member 1316b as shown in FIG. 23. In the extended position, the outer member flange will be disposed at a distal end of the passage of knob 1336 to maintain the outer member 1314 in the extended position during penetration of anatomical tissue, and the hub body portion 1359 has an internal configuration to permit proximal movement of outer member 1314 from the extended position to a retracted position as shown in FIG. 25 to increase the separation distance between expandable members 1316a and 1316b. With the end portion 1357 of hub 1318 coupled with the body portion 1359, the penetrating member P is disposed within the inner member 1312 such that the penetrating member tip 1339 protrudes distally beyond the distal end 1320 of inner member 1312 and the inner and outer members form a portal sleeve for penetrating member P FIGS. 26–29 illustrate use of instrument 1310 in extraperitoneal inguinal hernia repair. As shown in FIG. 26, the penetrating member P is inserted beneath the skin and subcutaneous fat F' forming wall W in the inguinal region. Prior to or subsequent to insertion of instrument 1310 into wall W, the outer member 1314 can be moved to the retracted position to increase the distance between expandable members 1316a and 1316b in accordance with procedural use. FIG. 26 illustrates outer member 1314 moved to the retracted position subsequent to penetration of wall W by penetrating member P to position instrument 1310 along side a herniated bowel B with expandable members 1316a and 1316b at opposite ends of herniated bowel B. Once the expandable members 1316a and 1316b have been properly positioned, fluid is supplied via supplemental inlet ports 1380a and 1380b to move the expandable members 1316a and 1316b, respectively, to the expanded position, and the penetrating member P is withdrawn. By controlling the amount of fluid supplied to the expandable members, the expandable members 1316a and 1316b can be expanded to different sizes as shown in FIG. 27. Movement of expandable members 1316a and 1316b to the expanded position causes an initial space $S^1$ to be created between the layers forming wall W, and the space between expandable members 1316a and 1316b defines space $S^1$.

Figure 28:
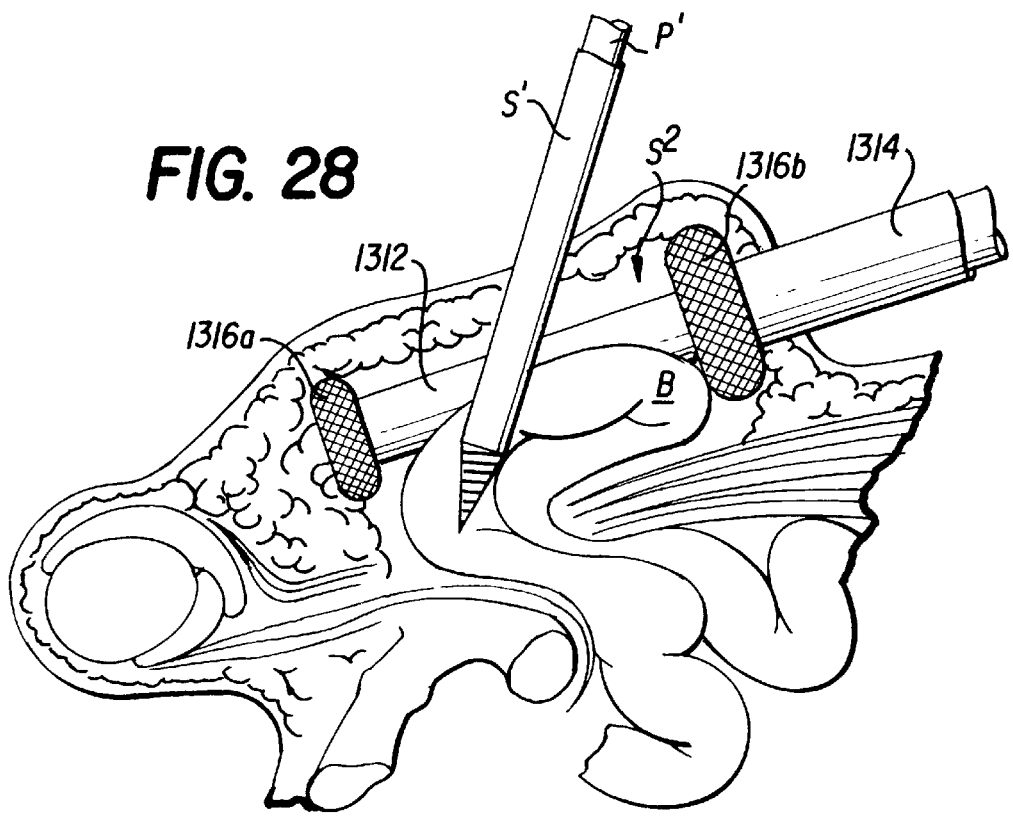
FIG. 28 is a broken perspective view illustrating the expandable members of the expandable multifunctional instrument of FIG. 27 creating a second larger space at the obstructed site and an additional portal sleeve placed in communication with the second space.
Figure 29:
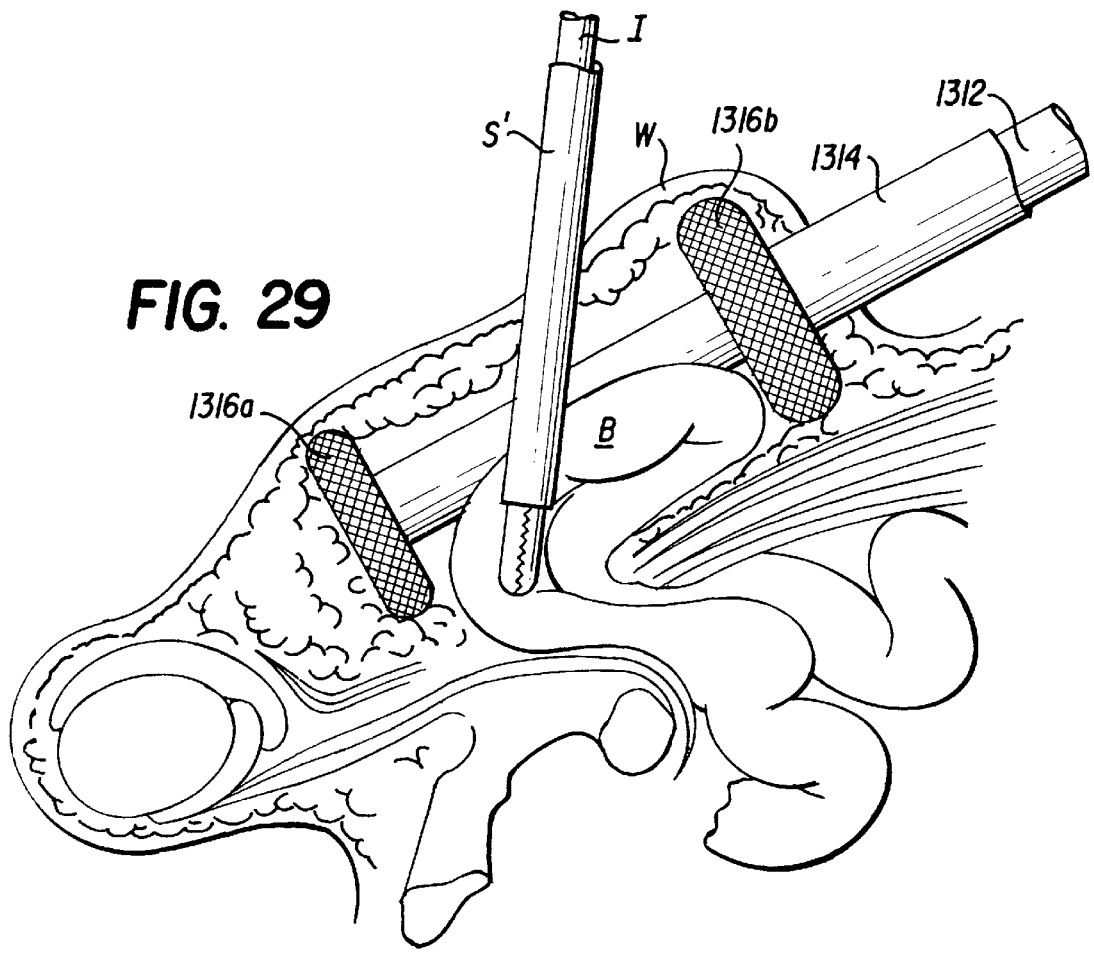
FIG. 29 is a broken perspective view illustrating an instrument introduced through the additional portal sleeve of FIG. 28.

As shown in FIG. 28, additional fluid can be supplied to expandable members 1316a and 1316b to increase the size of the expandable members to create a second larger space $S^2$. Alternatively, in conjunction with or in addition to further expansion of expandable members 1316a and 1316b, the second space $S^2$ can be created in the various ways previously described herein. In multiple puncture procedures, an additional penetrating instrument including a penetrating member P' and a portal sleeve S' is introduced into wall W to position the portal sleeve S' in communication with the thusly created operating space $S^2$. Once the portal sleeve S' is properly positioned, the penetrating member P' is withdrawn therefrom allowing various additional instruments I, such as a forceps, to be introduced at the operating space for use in repairing the hernia as shown in FIG. 29. Once the final operating space has been created, the hernia is repaired via instruments introduced through instrument 1310 or through additional portals, and the hernia can be repaired by securing a mesh to the bowel.

Figure 30:
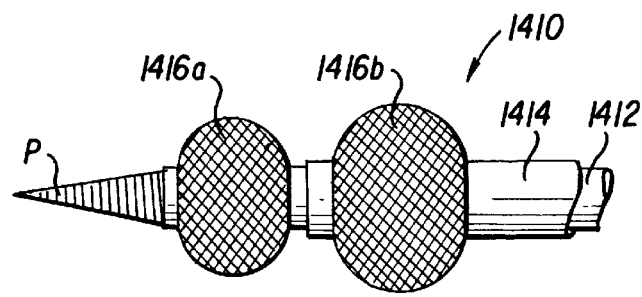
FIG. 30 is a broken side view of a distal portion of another modification of an expandable multifunctional instrument according to the present invention.

FIG. 30 illustrates at 1410 a distal portion of a modification of an expandable multifunctional instrument according to the present invention. Instrument 1410 is similar to instrument 1310 except that expandable members 1416a and 1416b are made from a non-elastic, non-stretchable material, such as plastic.

Figure 31:
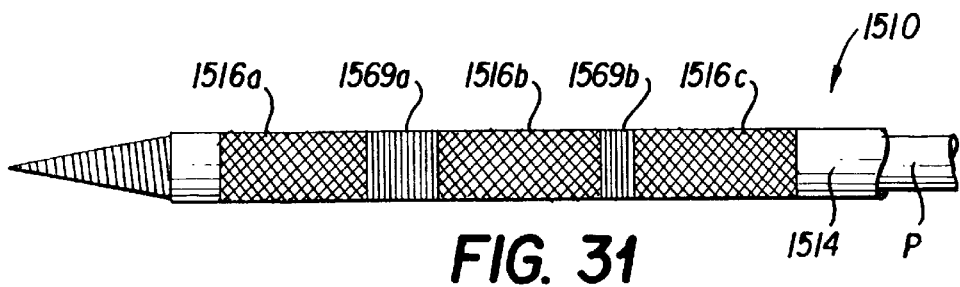
FIG. 31 is a broken side view of a distal portion of an additional modification of an expandable multifunctional instrument according to the present invention.

Another modification of an expandable multifunctional instrument according to the present invention is illustrated at 1510 in FIG. 31 wherein only a distal portion of the instrument 1510 is shown. Instrument 1510 is similar to instrument 1310 except that instrument 1510 includes a single outer member 1514 receiving penetrating member P. Outer member 1514 is similar to outer member 1314 except that outer member 1514 includes one or more adjustable collars 1569 disposed over expandable member 1516 to form a plurality of expandable member portions. Instrument 1510 has two collars 1569a and 1569b of different sizes disposed over expandable member 1516 to form expandable member portions 1516a, 1516b and 1516c with expandable member portions 1516a and 1516b being separated from one another by a distance that is greater than the distance that expandable member portions 1516b and 1516c are separated from one another. Various structure and arrangement of expandable multifunctional instruments having adjustable collars are shown in the prior applications.

Figure 32:
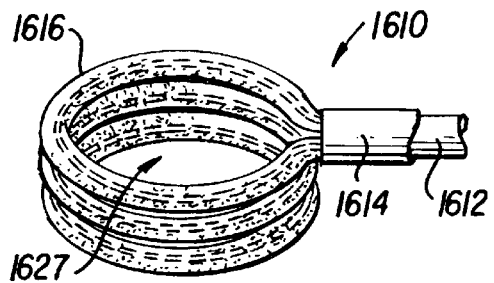
FIG. 32 is a broken perspective view of a distal portion of still a further modification of an expandable multifunctional instrument according to the present invention.

Another modification of an expandable multifunctional instrument according to the present invention is illustrated at 1610 in FIG. 32 wherein only a distal portion of the instrument 1610 is shown. Instrument 1610 includes outer member 1614 and inner member 1612 carrying expandable member 1616 which is made of an absorbent material such as sponge or gauze. Expandable member 1616 has a first configuration in a non-expanded position wherein the expandable member is in a dry state to be disposed within outer member 1614 and a second configuration in an expanded position wherein the expandable member is in a wet state. Expandable member 1616 in the non-expanded position is in the nature of a sponge or gauze stick and has a coiled configuration in the expanded position defining a cylindrical operating space 1627. Expandable member 1616 is particularly useful for being disposed around tissue or organ structure and for lifting or otherwise manipulating tissue or organ structure to create a space at an obstructed site. Expandable member 1616 is moved to the expanded position upon retraction of outer member 1614 to expose the expandable member 1616 in the body. The expandable member can be moved to the expanded position fluidically via absorption of body fluid by the absorbent material or via fluid supplied to the expandable member and/or mechanically as previously described herein. A spine can be provided externally of, internally of or within the material forming the expandable member 1616 for shaping or rigidifying the expandable member and/or for mechanically moving the expandable member to the expanded position. Where a spine is provided, the spine can be utilized to supply fluid and/or medicinal or therapeutic substances, and fluid can be aspirated from the expandable member through the spine to facilitate withdrawal from the body. Various expandable members made of absorbent material and having use in the present invention are disclosed in applicant's prior applications Ser. No. 07/600,775 filed Oct. 23, 1990 and Ser. No.

07/556,081 filed Jul. 24, 1990, the disclosures of which are incorporated herein by reference.

Figure 33:
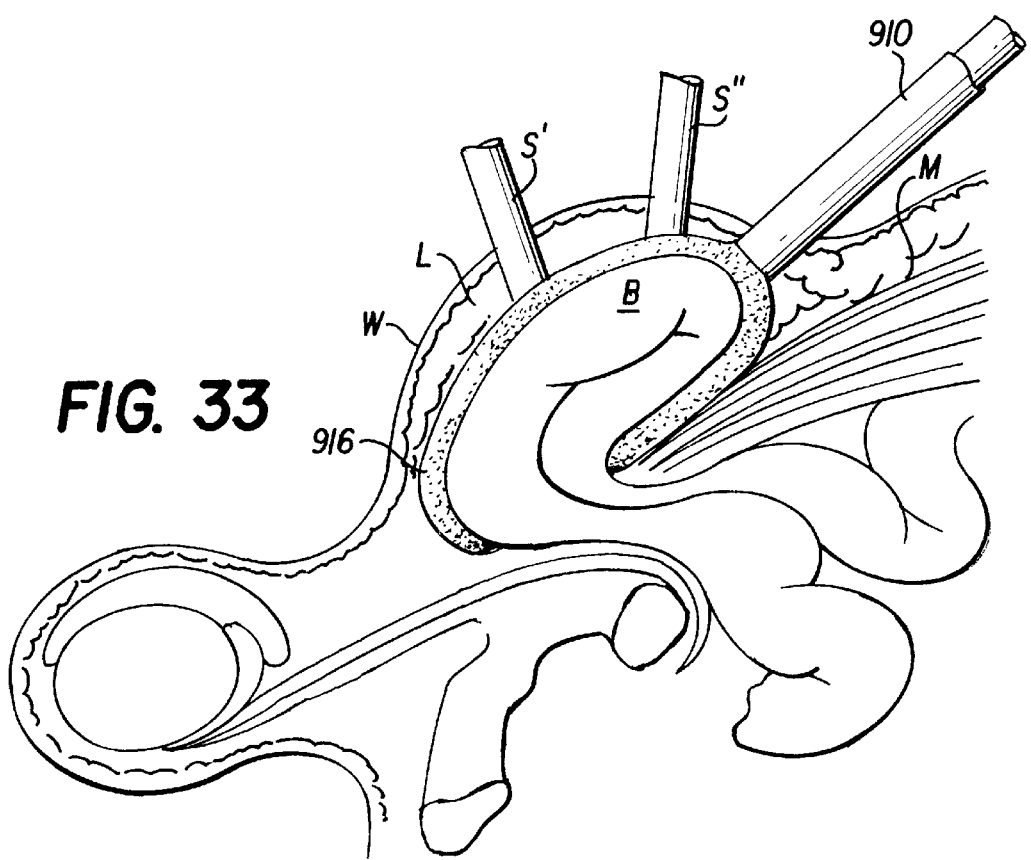
FIG. 33 is a broken perspective view illustrating use of the expandable multifunctional instrument of FIG. 17 in preperitoneal endoscopic direct hernia repair.
Figure 34:
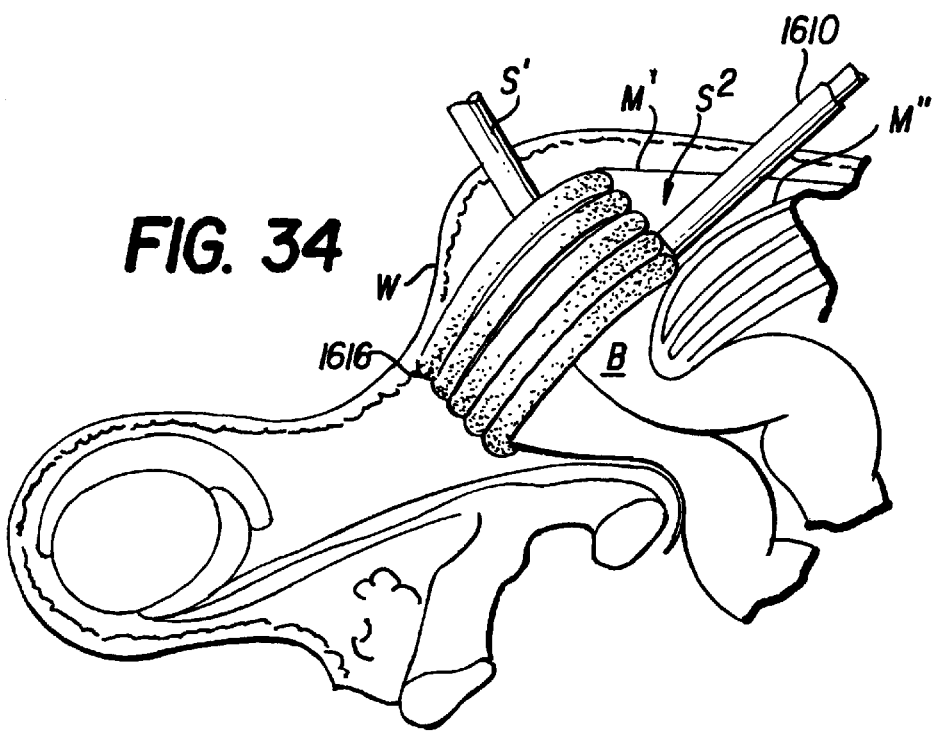
FIG. 34 is a broken perspective view illustrating use of the expandable multifunctional instrument of FIG. 22 in intraperitoneal endoscopic direct hernia repair.
Figure 35:
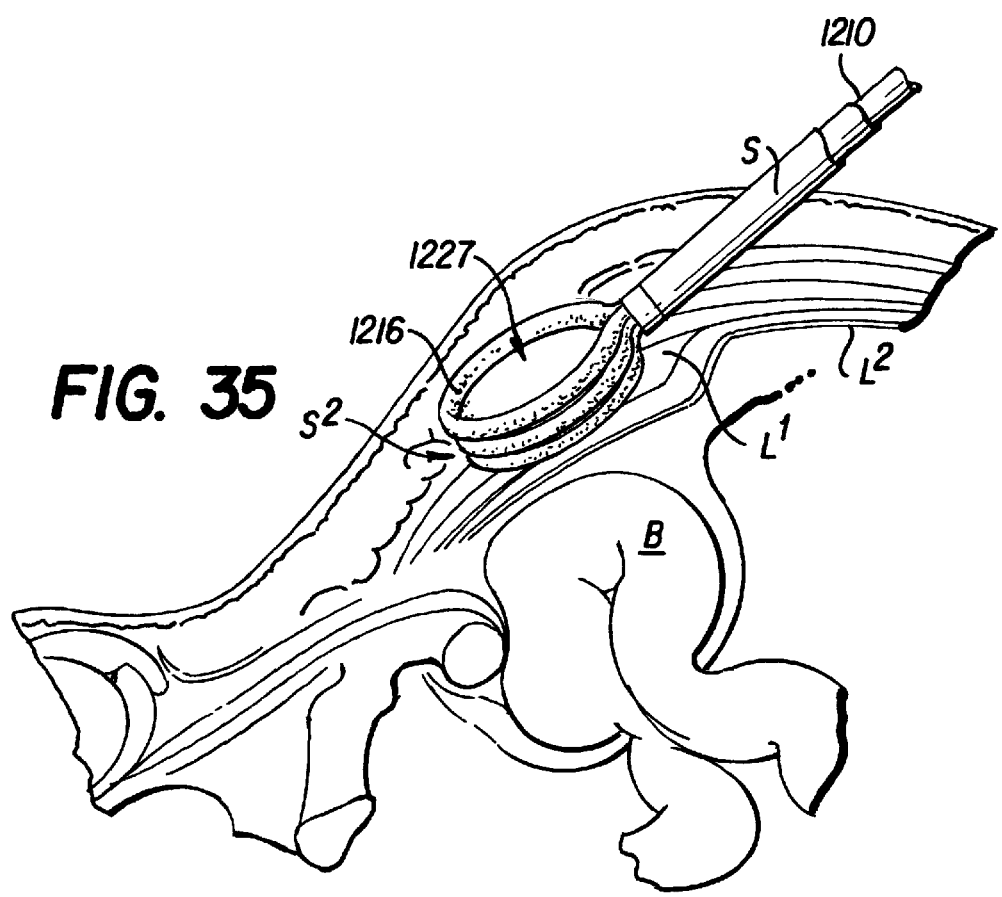
FIG. 35 is a broken perspective view illustrating use of the expandable multifunctional instrument of FIG. 32 in extraperitoneal endoscopic direct hernia repair.

FIGS. 33–35 illustrate expandable multifunctional instruments according to the present invention in use in various operative procedures. FIG. 33 illustrates instrument 910 in use in a three puncture procedure of preperitoneal endoscopic direct hernia repair. Expandable member 916 is positioned along side herniated bowel B between the superficial fascia L and the external oblique muscle M of wall W and is moved to the expanded position to create an operating space between the layers of wall W proparietal or extraparietal with the bowel B being held in a cupping manner within the working space 927 of the expandable member 916. Portal sleeves S' and S" are positioned in the wall W in communication with the thusly created operating space allowing various instruments to be introduced therethrough for use in repairing the hernia. The instrument 910 can be introduced into wall W via a portal sleeve (not shown).

FIG. 34 illustrates instrument 1610 in use in an intraperitoneal endoscopic direct hernia repair procedure. The expandable member 1616 is positioned adjacent the herniated bowel B between the internal and external oblique muscles M' and M", respectively, of wall W and the instrument 1610 can be introduced through a portal sleeve (not shown). The expandable member 1616 is moved to the expanded position M to create an operating space $S^2$ interparietal with the coiled configuration of the expandable member separating adjacent layers of wall W to create space $S^2$ and provide an operating opening for receiving bowel B in a cupping manner and/or providing an area for performing operative procedures. FIG. 34 illustrates a two puncture technique in that an additional portal sleeve S' is inserted in wall W to allow various instruments or fluid to be introduced at the operating space.

FIG. 35 illustrates expandable multifunctional instrument 1210 in use in extraperitoneal endoscopic direct hernia repair. Expandable member 1216 is positioned between the transversa fascia $L^1$ and the peritoneum $L^2$ and is moved to the expanded position to create an operating space $S^2$ retroparietal or intraparietal between layers $L^1$ and $L^2$. Various additional instruments or fluid can be introduced through the working channel of instrument 1210 to repair the herniated bowel B via the operating space 1227.

Figure 36:
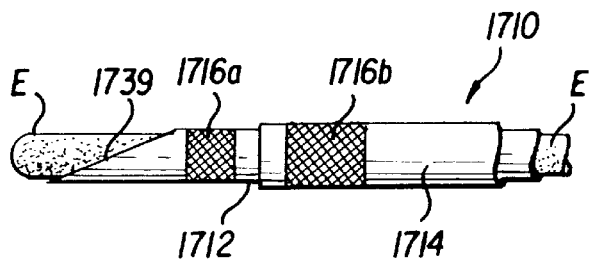
FIG. 36 is a broken side view of a distal portion of a further modification of an expandable multifunctional instrument according to the present invention.

Another modification of an expandable multifunctional instrument according to the present invention is illustrated in FIG. 36 at 1710, only the distal portion of instrument 1710 being shown. Expandable multifunctional instrument 1710 is similar to expandable multifunctional instrument 1310 except that penetrating member P, which carries expandable member 1716*a*, is cannulated or hollow with an angled distal tip 1739. A remote visualization device such as an endoscope E is disposed within the penetrating member P with an image receiving distal end of the endoscope positioned relative to distal tip 1739 to provide visualization at the distal end of instrument 1710. Use of instrument 1710 is similar to that previously described except that endoscope E is introduced in the body along with penetrating member P to visually identify and locate the potential space or proper site for creation of the actual initial space. In this manner, the surgeon will know when the potential space has been reached at the obstructed site, and thereafter the expandable member 1716*a* and/or the expandable member 1716*b* carried by outer member 1714 is moved to the expanded position to create an actual space at the obstructed site. Depending on the configuration of penetrating member P, the visualization device can fill the lumen of the penetrating member or be disposed in a channel or passage of the penetrating member or along side the penetrating member aligned with or non-aligned with a longitudinal axis of the penetrating member.

Figure 37:
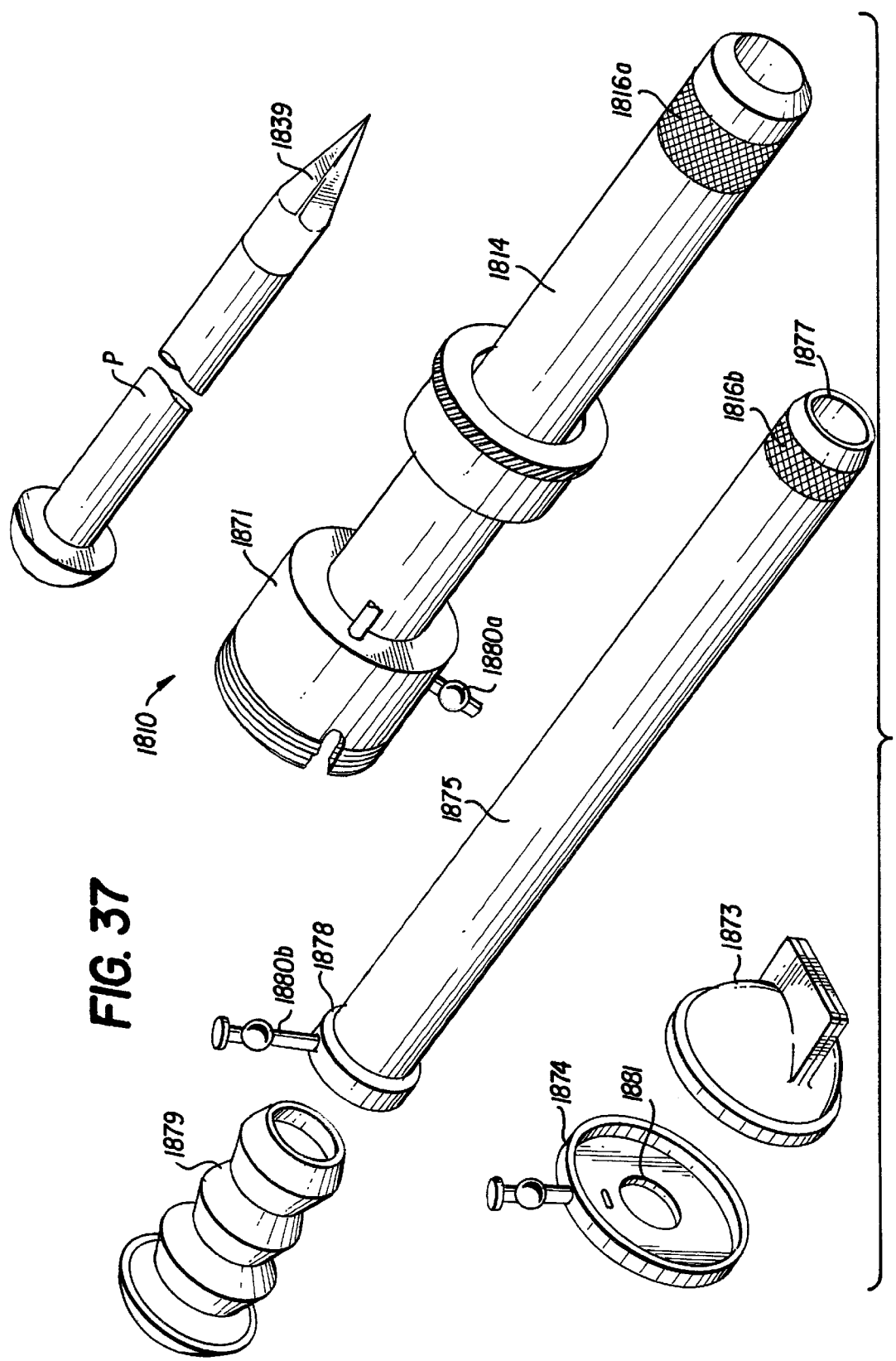
FIG. 37 is an exploded perspective view of another modification of an expandable multifunctional instrument according to the present invention.

FIG. 37 illustrates at 1810 a further modification of an expandable multifunctional instrument according to the present invention. Instrument 1810 is similar to instrument 1310 and includes an outer member 1814 terminating distally at a distal end 1834 and proximally at an enlarged threaded coupling 1871 having an open rearward end. A valve assembly, such as a nipple valve 1873, is mounted in the coupling 1871 to prevent undesired fluid flow through outer member 1814. An internally threaded annular cap 1874 is mounted on the rearward end of coupling 1871 in engagement with the thread thereon. An elongate, tubular middle member 1875 is disposed in outer member 1814 and terminates distally at a distal end 1877 and proximally at a flange 1878. A compression spring 1879 is mounted in coupling 1871 in engagement with flange 1878 to bias the middle member 1875 distally. Expandable member 1816*a* is carried by outer member 1814 which is of hollow, double-wall construction defining a passage between outer and inner walls thereof coupling expandable member 1816*a* with inlet port 1880*a* disposed along coupling 1871. Middle member 1875 carries expandable member 1816*b* and is similarly constructed of hollow, double-wall construction to define an interior passage coupling expandable member 1816*b* with inlet port 1880*b* disposed on flange 1878. A penetrating member P is disposed in middle member 1875 through an opening 1881 in cap 1874 and terminates distally at a faceted tip 1839 for penetrating anatomical tissue. With the components of instrument 1810 assembled, the tip 1839 of the penetrating member will protrude distally beyond the distal end 1834 of the outer member 1814 and the middle member 1875 will be biased to protrude distally beyond the distal end 1834 of the outer member 1814 such that expandable member 1816*b* will be disposed distally of expandable member 1816*a*. During penetration of anatomical tissue, middle member 1875 will be moved proximally against the bias of spring 1879 and, upon a reduction in force from tissue contact at a distal end of instrument 1810, the middle member 1875 will move distally to position expandable member 1816*b* distally of expandable member 1816*a*. It should be appreciated that automatic distal movement of middle member 1875 can be obtained where the nature of the tissue at the obstructed site is such as to reduce the force from tissue contact at a distal end of the instrument 1810 to allow automatic protrusion of the middle member 1875; however, various structure can be provided in the instrument 1810 to allow extension of the middle member 1875 manually, selectively when the potential space is reached. Once the instrument 1810 is properly positioned at the potential space with expandable member 1816*b* disposed distally of expandable member 1816*a*, the expandable members are utilized to create an actual initial space and operating space as described previously above.

The expandable multifunctional instruments according to the present invention can include any number of inner, middle and/or outer members concentrically or non-concentrically disposed and any number of expandable members. The expandable members can be carried on any of the inner members, middle members and/or outer members and can be made of stretchable, elastic material, non-stretchable or non-elastic material, absorbent material or any combination thereof. Where absorbent materials are utilized, the expandable members can be utilized to absorb bodily fluids, such as blood, for enhanced visualization and/or performance of operative procedures. Where the expandable members are carried by the outer members, the outer members can define portal sleeves for receiving penetrating members for penetrating tissue to introduce the expandable members at obstructed sites.

The expandable members can be provided with or without various spines for maintaining the shape of the expandable members in the expanded position, for providing rigidity to the expandable members and/or for moving the expandable members to the expanded position. The spines can be disposed externally of, internally of or within the material of the expandable members. The spines can extend entirely through the instruments or partially through the instruments, and the spines can be hollow or tubular to allow fluid flow through the spines.

The expandable members can be moved to the expanded position fluidically via inflation or via absorption of body fluids or fluids supplied to the expandable members, mechanically or any combination thereof. Where the expandable members are moved to the expanded position fluidically, fluid can be supplied through the inner members, middle members, spines, control tubes, between the inner members and the control tubes, between the inner members and the spines, through the outer members and/or through separate fluid passages coupling the expandable members with the inlet ports.

The expandable members can be continuously expandable to different sizes or can have various predetermined sizes in the expanded position. The expandable members can have various predetermined or preformed configurations or shapes in the expanded position in accordance with procedural use including various shapes for holding or manipulating tissue and defining or circumscribing various working or operating spaces. Some configurations for the expandable members that are particularly advantageous include triangular, toroid, round, multiple finger, J-shaped, annular or donut-shaped, C-shaped, U-shaped, spoon-shaped, oval, single or multiple ball-shaped and coiled configurations. With the use of certain shapes, such as multiple finger shapes, the expandable members can be used to retract or expose anatomical tissue. The expandable members can be invertible to continuously roll or invert when instruments are passed therethrough as disclosed in prior application Ser. No. 08/220,359, filed Mar. 31, 1994, the disclosure of which is incorporated herein by reference.

The expandable members can be disposed within the outer members to be unexposed during introduction in the body and/or to be maintained in a non-expanded position. The outer members are movable from an extended position to a retracted position to expose the expandable members, to permit movement of the expandable members to the expanded position and/or to increase the space or distance between multiple expandable members. The expandable members can be moved to the expanded position automatically in response to retraction of the outer members. Where multiple expandable members are provided, the distance or separation between the expandable members can be selectively adjusted with the use of relatively movable inner and outer members or with the use of adjustable collars. The angular orientation of the expandable members can be adjusted, and the expandable members can be articulated angularly via various spring mechanisms, wire adjustment systems, predetermined bent members and two-coiled tubing. The expandable members can be aligned with the longitudinal axes of the instruments of offset therefrom. The working or operating passages of the expandable members can be aligned with the longitudinal axes of the expandable members of offset therefrom. The expandable multifunctional instruments can be designed in many various ways to permit drainage through the instruments.

According to the present invention, initial spaces are created at obstructed sites by introducing or injecting fluid under pressure at the obstructed site or by expanding expandable members at the obstructed sites. In particular, fluid can be introduced at obstructed sites in areas such as the breast, lung, brain, structure adjacent embolic or anuretic arteries or veins, retroperitoneal spaces, layers of the spinal cord, preperitoneal spaces for ventral hernia or inguinal hernia repair, subcutaneous tissue for removal of ganglia, benign lumps or melanoma, bowel or bowel wall, liver, spleen, pancreas, kidney, gall bladder, uterine wall, the space of Retzius utilizing liquids, and pathological locations and locations adjacent pathological locations. Upon creation of the initial spaces second spaces can be created by expanding expandable members at the initial spaces, by moving expanded expandable members at the initial spaces and/or by introducing fluid at the initial spaces. The initial spaces can be of a size just large enough to permit visual observation such that the second spaces, which can be large enough in size to provide sufficient room for performing operative procedures, can be created subsequent to visual confirmation of the proper location of the initial spaces. Accordingly, if the initial spaces are not at the proper location, connective measures can be taken without excessively large spaces having been formed. The thusly created operating spaces can be maintained by leaving the expandable multifunctional instruments in place or by withdrawing the expandable multifunctional instruments and introducing fluid at the operating spaces. Where left in place, the expandable members prevent withdrawal of the instruments from the body allowing the instruments to be used as portal sleeves without the risk of backing out from the body.

According to the present invention, creation of the initial and second spaces as well as procedures conducted prior and subsequent thereto can be visualized using remote visualization devices. Fluid introduced for insufflation, to create spaces or for treatment procedures can be supplied via the expandable multifunctional instruments, via the remote viewing devices, or via separate instruments and/or portals. The expandable multifunctional instruments can be introduced in the body via various single or multiple portals, via the remote viewing devices or via instruments used to supply fluid. Various penetrating members can be used in the expandable multifunctional instruments for simultaneous penetration and positioning of the instruments in the body. By using remote viewing devices along with the penetrating members, the obstructed sites can be located visually for confirmation of penetration of the instruments to the desired depth or layer. Various additional instruments can be introduced in the body via the expandable multifunctional instruments or via separate portals, such additional instruments including dissecting instruments, scissors, combination biopsy and scissors instruments, forceps, suturing instruments, needle and suture needle holders, suction instruments, cutting instruments, combination suction and cutting instruments, clip applicators, ring applicators, coagulating instruments, cautery instruments and sponge sticks as well as other multifunctional expandable instruments. Various procedures can be performed according to the present invention utilizing single or multiple puncture techniques. The present invention is particularly useful in hernia repair including repair of direct, indirect, encysted, funicular, vaginal and infantile hernias without entry into the abdomen. In addition to the areas previously described herein, other areas where the present invention is useful include liposuction, ileostomy, jejunostomy, colostomy and anastomic procedures.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An expandable multifunctional instrument for creating a space endoscopically at an obstructed site in anatomical tissue in the body, comprising:

a hollow elongate member having a distal end for being positioned at the obstructed site and a proximal end for being held externally of the body, the hollow elongate member defining an operating channel extending between the distal and proximal ends;

an expandable member carried at said distal end of said hollow elongate member, said expandable member being movable from a non-expanded position to an expanded position to separate the anatomical tissue to create a space at the obstructed site, said expandable member including a balloon movable fluidically from said non-expanded position to said expanded position, said balloon assuming a preformed, predetermined configuration in said expanded position at the obstructed site;

a penetrating member disposed in the operating channel and extending beyond the expandable member for penetrating the anatomical tissue to introduce the expandable member at the obstructed site; and an outer tubular member receiving said hollow elongate member and an outer tubular expandable member carried by said outer tubular member, at least one of said outer tubular member and said hollow elongate member being movable relative to the other of said outer tubular member and said hollow elongate member to position said outer tubular member in an extended position wherein said expandable member is separated from said outer tubular expandable member by a separation distance and to permit movement of said outer tubular member to a retracted position wherein said hollow expandable member is separated from said outer tubular expandable member by a second greater separation distance.

2. An expandable multifunctional instrument for creating a space endoscopically at an obstructed site in anatomical tissue in the body comprising a hollow elongate member having a distal end for being positioned at the obstructed site and a proximal end for being held externally of the body, the hollow elongate member defining an operating channel extending between the distal and proximal ends;

an expandable member carried at said distal end of said elongate member, said expandable member being movable from a non-expanded position to an expanded position to separate the anatomical tissue to create a space at the obstructed site, said expandable member including a balloon movable fluidically from said non-expanded position to said expanded position, said balloon assuming a preformed, predetermined configuration in said expanded position at the obstructed site; and an outer tubular member receiving said elongate member and an outer tubular expandable member carried by said outer tubular member, at least one of said outer tubular member and said elongate member being movable relative to the other of said outer tubular member and said elongate member to position said outer tubular member in an extended position wherein said expandable member is separated from said outer tubular expandable member by a separation distance and to permit movement of said outer tubular member to a retracted position wherein said expandable member is separated from said outer tubular expandable member by a second greater separation distance; and a penetrating member disposed in the operating channel and extending beyond the expandable member for penetrating the anatomical tissue to introduce the expandable member at the obstructed site.

3. The expandable multifunctional instrument as recited in claim 2 wherein said expandable member has a multiple finger configuration in said expanded position.

4. An expandable multifunctional instrument for creating a space endoscopically at an obstructed site in anatomical tissue in the body, comprising:

a hollow elongate member having a distal end for being positioned at the obstructed site and a proximal end for being held externally of the body, the hollow elongate member defining an operating channel extending between the distal and proximal ends;

an expandable member carried at said distal end of said hollow elongate member, said expandable member being movable from a non-expanded position to an expanded position to separate the anatomical tissue to create a space at the obstructed site, said expandable member including a balloon movable fluidically from said non-expanded position to said expanded position, said balloon assuming a preformed, predetermined configuration in said expanded position at the obstructed site, said expandable member having a multiple finger configuration in the expanded position; and a penetrating member disposed in the operating channel and extending beyond the expandable member for penetrating the anatomical tissue to introduce the expandable member at the obstructed site.

* * * * *